United States Patent
Overmyer et al.

(10) Patent No.: US 11,033,344 B2
(45) Date of Patent: Jun. 15, 2021

(54) IMPROVING SURGICAL TOOL PERFORMANCE VIA MEASUREMENT AND DISPLAY OF TISSUE TENSION

(71) Applicant: Ethicon LLC, Guaynabo, PR (US)

(72) Inventors: Mark D. Overmyer, Cincinnati, OH (US); Sol A. Posada, Lansdale, PA (US); Joshua D. Young, Loveland, OH (US); Mark A. Davison, Maineville, OH (US); Christopher A. Denzinger, Cincinnati, OH (US)

(73) Assignee: Cilag GmbH International

( * ) Notice: Subject to any disclaimer, the term of this patent is extended or adjusted under 35 U.S.C. 154(b) by 244 days.

(21) Appl. No.: 16/219,050

(22) Filed: Dec. 13, 2018

(65) Prior Publication Data

US 2020/0188045 A1 Jun. 18, 2020

(51) Int. Cl.
| | |
|---|---|
| A61B 34/35 | (2016.01) |
| A61B 34/00 | (2016.01) |
| A61B 17/29 | (2006.01) |
| A61B 34/30 | (2016.01) |
| A61B 17/072 | (2006.01) |

(52) U.S. Cl.
CPC ............ *A61B 34/35* (2016.02); *A61B 17/29* (2013.01); *A61B 34/76* (2016.02); *A61B 34/77* (2016.02); *A61B 17/072* (2013.01); *A61B 2017/2927* (2013.01); *A61B 2034/305* (2016.02); *A61B 2034/741* (2016.02); *A61B 2034/742* (2016.02); *A61B 2034/743* (2016.02); *A61B 2034/744* (2016.02)

(58) Field of Classification Search
CPC ................................ A61B 34/76; A61B 34/77
See application file for complete search history.

(56) References Cited

U.S. PATENT DOCUMENTS

| | | | | |
|---|---|---|---|---|
| 5,383,880 | A * | 1/1995 | Hooven | A61B 17/072 227/175.1 |
| 8,716,973 | B1 * | 5/2014 | Lammertse | B25J 9/1694 318/671 |
| 2007/0151390 | A1 * | 7/2007 | Blumenkranz | B25J 15/0009 74/490.06 |
| 2008/0051629 | A1 * | 2/2008 | Sugiyama | A61B 1/018 600/114 |
| 2011/0046637 | A1 * | 2/2011 | Patel | A61B 17/29 606/130 |
| 2011/0118778 | A1 * | 5/2011 | Burbank | A61B 17/07207 606/205 |
| 2014/0067123 | A1 * | 3/2014 | Park | G01L 1/246 700/258 |
| 2015/0238276 | A1 | 8/2015 | Atarot et al. | |
| 2016/0354164 | A1 | 12/2016 | Nichogi et al. | |
| 2017/0189130 | A1 * | 7/2017 | Weir | A61B 34/37 |
| 2019/0200998 | A1 * | 7/2019 | Shelton, IV | A61B 1/0661 |
| 2020/0188046 | A1 * | 6/2020 | Overmyer | A61B 34/25 |

* cited by examiner

*Primary Examiner* — Alexander J Orkin
(74) *Attorney, Agent, or Firm* — Vorys, Sater, Seymour and Pease LLP

(57) ABSTRACT

A method includes advancing an end effector of a surgical tool to a surgical site, the surgical tool being pivotably mounted to a robotic arm at a tool driver, engaging tissue at the surgical site with the end effector, calculating a force vector assumed on the end effector by engaging the tissue, optimizing the force vector to obtain an optimized force vector, and actuating the end effector after applying the optimized force vector on the end effector.

20 Claims, 16 Drawing Sheets

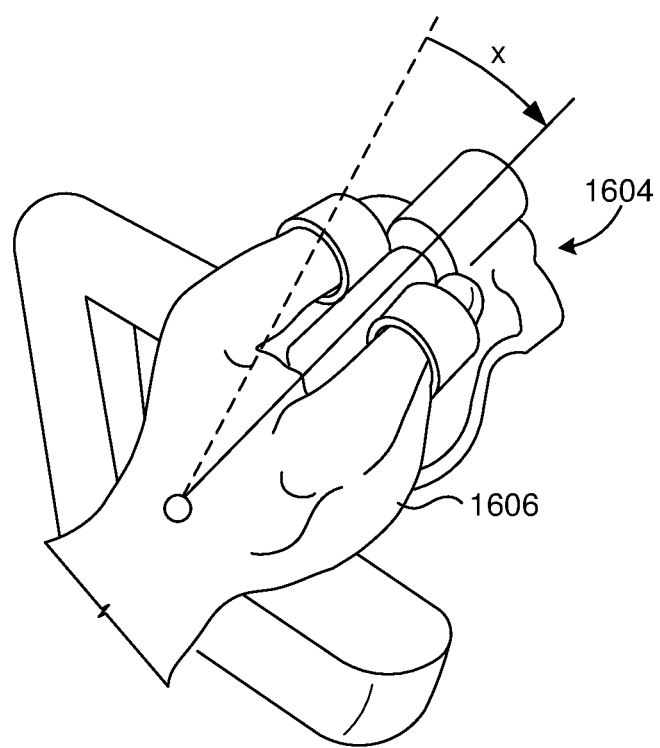
FIG. 16A
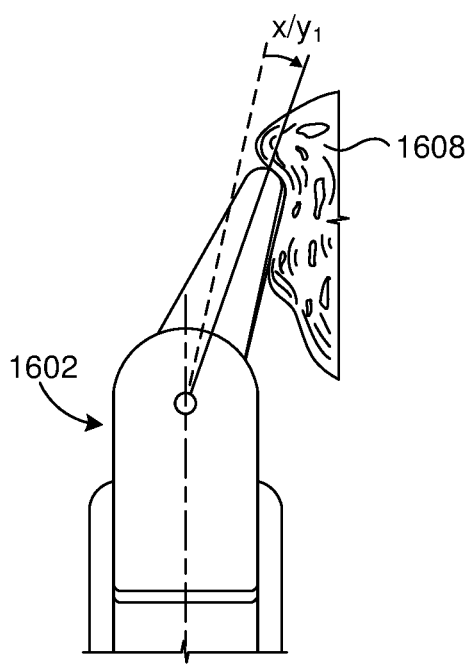 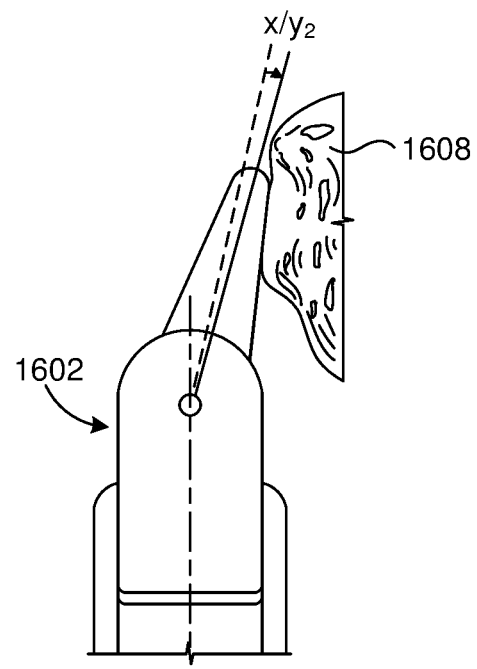
FIG. 16B  FIG. 16C

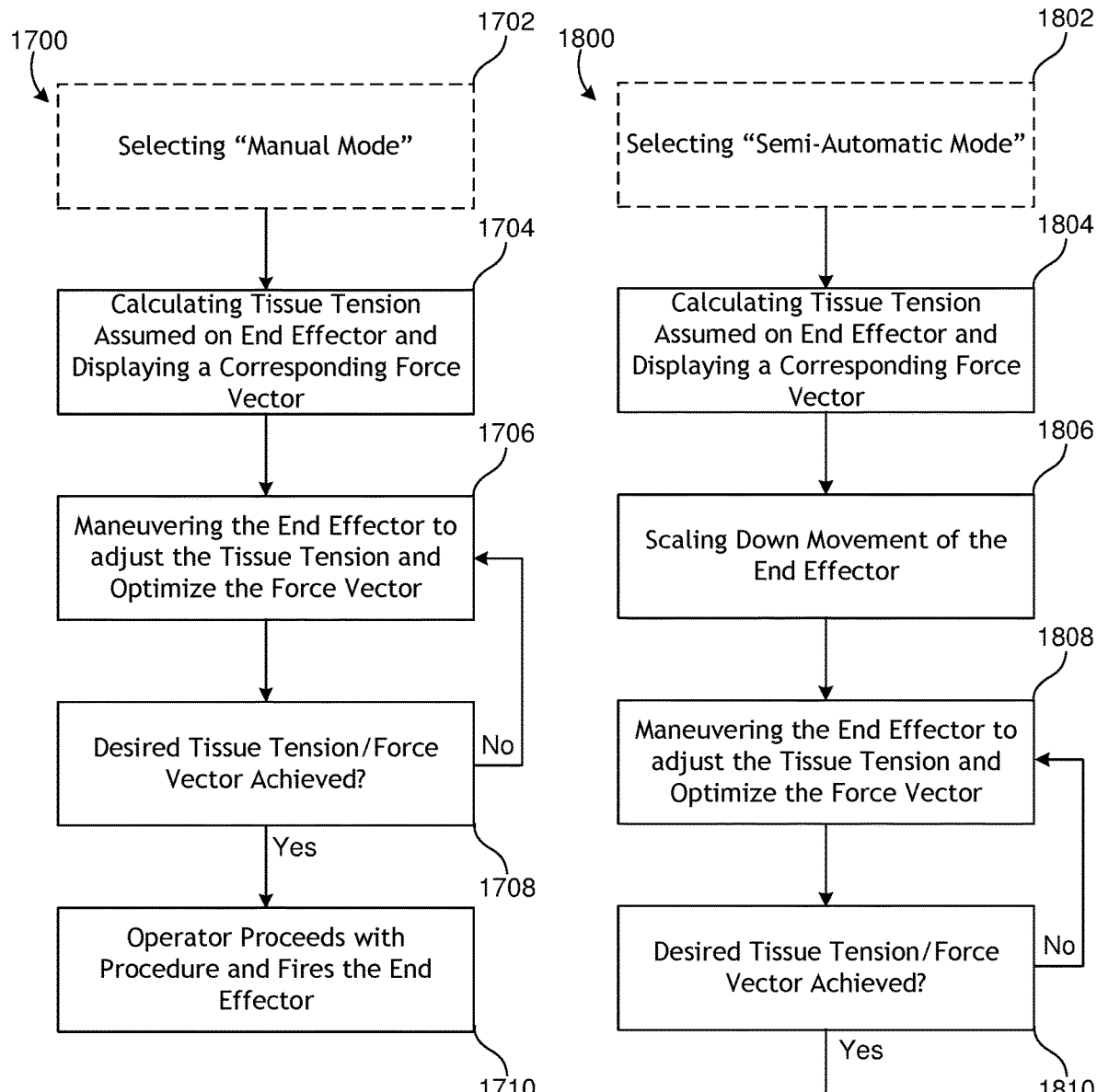

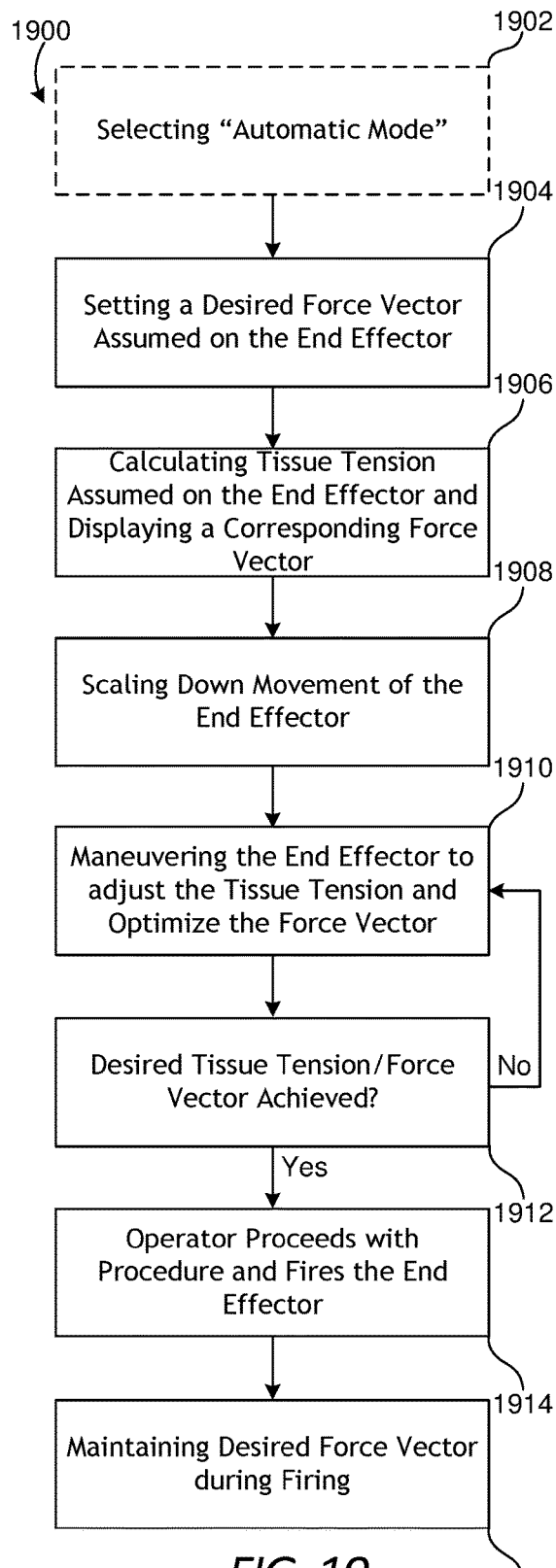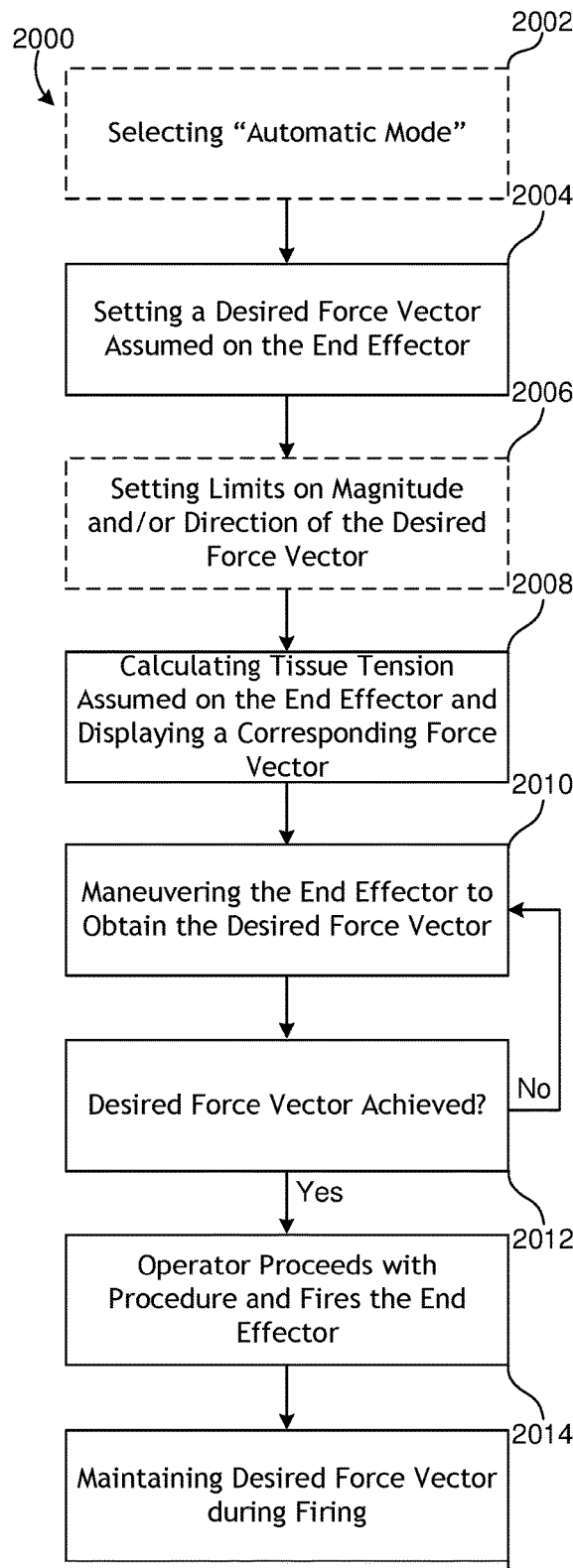
FIG. 19
FIG. 20

IMPROVING SURGICAL TOOL PERFORMANCE VIA MEASUREMENT AND DISPLAY OF TISSUE TENSION

BACKGROUND

Minimally invasive surgical (MIS) instruments are often preferred over traditional open surgical devices due to the reduced post-operative recovery time and minimal scarring. The most common MIS procedure may be endoscopy, and the most common form of endoscopy is laparoscopy, in which one or more small incisions are formed in the abdomen of a patient and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments can be used to engage and/or treat tissue in a number of ways to achieve a diagnostic or therapeutic effect.

Each surgical tool typically includes an end effector arranged at its distal end. Example end effectors include clamps, graspers, scissors, staplers, and needle holders, and are similar to those used in conventional (open) surgery, except that the end effector of each tool is separated from its handle by an approximately 12-inch long, shaft. A camera or image capture device, such as an endoscope, is also commonly introduced into the abdominal cavity to enable the surgeon to view the surgical field and the operation of the end effectors during operation. The surgeon is able to view the procedure in real-time by means of a visual display in communication with the image capture device.

Although traditional MIS surgical instruments and techniques have proven highly effective, newer systems provide even further advantages. For example, traditional MIS surgical instruments often deny the surgeon the flexibility of tool placement available in open surgery. Moreover, difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed on the visual display with actual end effector movement can be particularly difficult, since the movement as perceived in the image often does not correspond intuitively with actual end effector movement. Accordingly, lack of intuitive response to surgical instrument movement input is often experienced, and such a lack of intuitiveness, dexterity, and sensitivity of endoscopic tools has been found to be an impediment in the increased use of minimally invasive surgery.

Over the years a variety of minimally invasive robotic surgical systems have been developed to increase surgical dexterity as well as to permit a surgeon to operate on a patient in an intuitive manner. "Telesurgery" is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with one or more user input devices that remotely control one or more surgical tools. While viewing the surgical site on a visual display at a location remote from the patient, the surgeon is able to manipulate in space the user input devices to remotely control movement of the surgical tools. User inputs are processed by a computer system incorporated into the robotic surgical system, and the associated tool drivers and joints respond by articulating the end effector to desired angular positions and configurations.

While significant advances have been made in the field of robotic surgery, there remains a need for improved methods, systems, and devices for use in robotic surgery.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIGS. 16A-16C depict example operation of scaling down movement of an end effector, according to one or more embodiments.

FIGS. 17-20 are schematic flowcharts of example methods of optimizing loading on a surgical tool end effector, according to one or more additional embodiments.

DETAILED DESCRIPTION

The present disclosure is related to robotic surgery and, more particularly, to optimizing tissue tension on end effectors during actuation and preventing the end effectors from contacting critical bodily structures.

The embodiments described herein discuss systems and methods directed to managing and optimizing tissue tension without adversely affecting surrounding tissue. In some embodiments, for example, the presently described systems may be configured to reduce tissue tension to at or near zero and simultaneously eliminate any angular tension (torque) on the tissue. In embodiments where the end effector is a surgical stapler, the presently described systems may further be configured to create axially directed tension to mitigate the occurrence of a cutting element pushing tissue out of closed opposing jaws during firing. In other embodiments, however, the presently described systems may be configured to alter tissue tension to a desired (predetermined) tissue tension applied (delivered) in a particular direction. Such embodiments may prove advantageous with an end effector, such as scissors or an ultrasonic energy device, that operate more effectively when cutting through tissue in tension.

The embodiments described herein also discuss systems and methods directed to protecting critical bodily structures during minimally invasive surgical procedures. In at least one embodiment, an end effector of a surgical tool may be advanced to a surgical site, and images of the end effector and the surgical site may be captured with an image capture device. Such images may be displayed on a visual display. A restricted zone may be generated at the surgical site and may be positioned such that it interposes the end effector and a critical bodily structure. A computer system may be programmed to prevent the end effector from penetrating the restricted zone and thereby protecting the critical structure from contact with the end effector.

Figure 1:
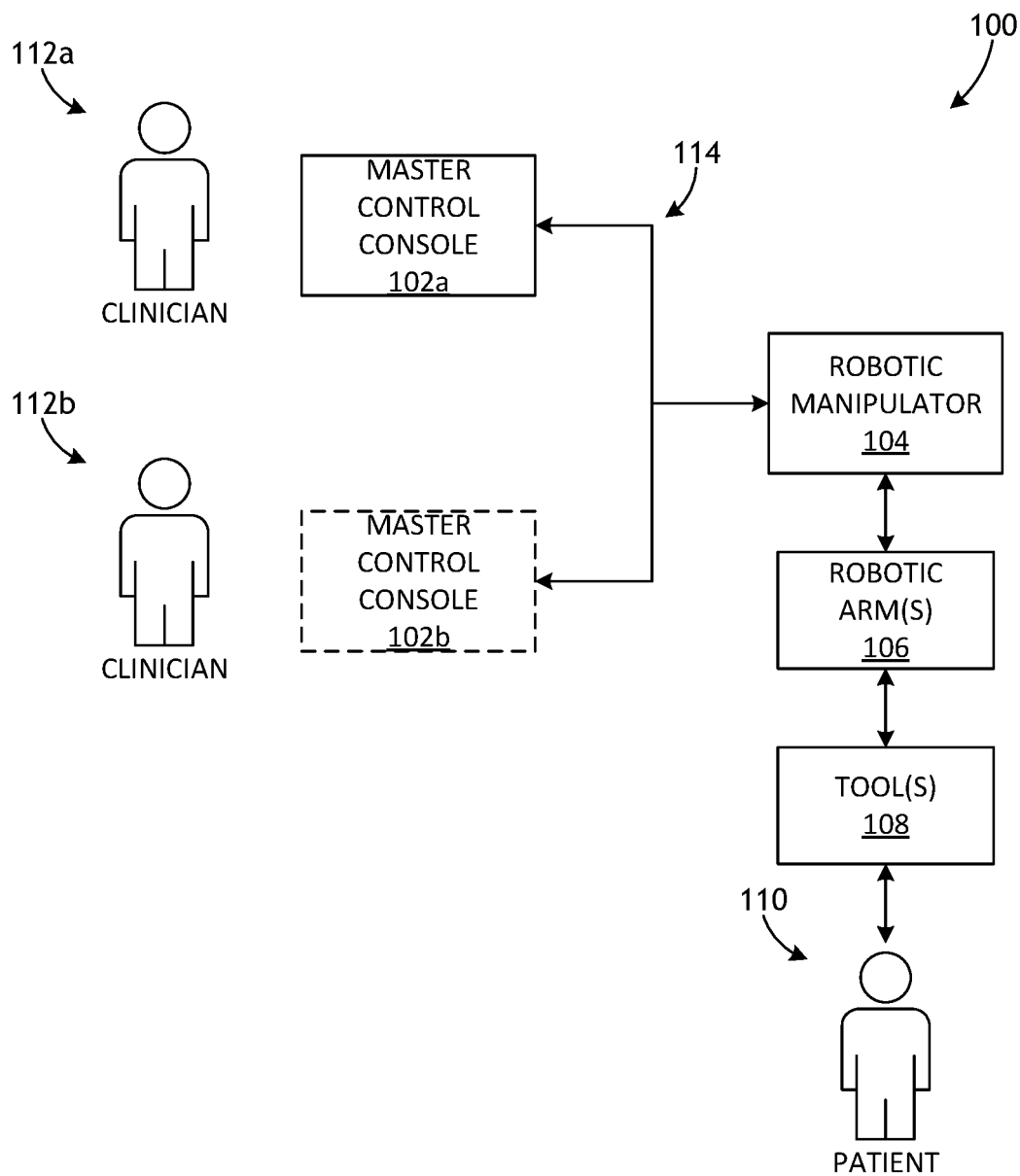
FIG. 1 is a block diagram of an example robotic surgical system that may incorporate some or all of the principles of the present disclosure.
Figure 3:
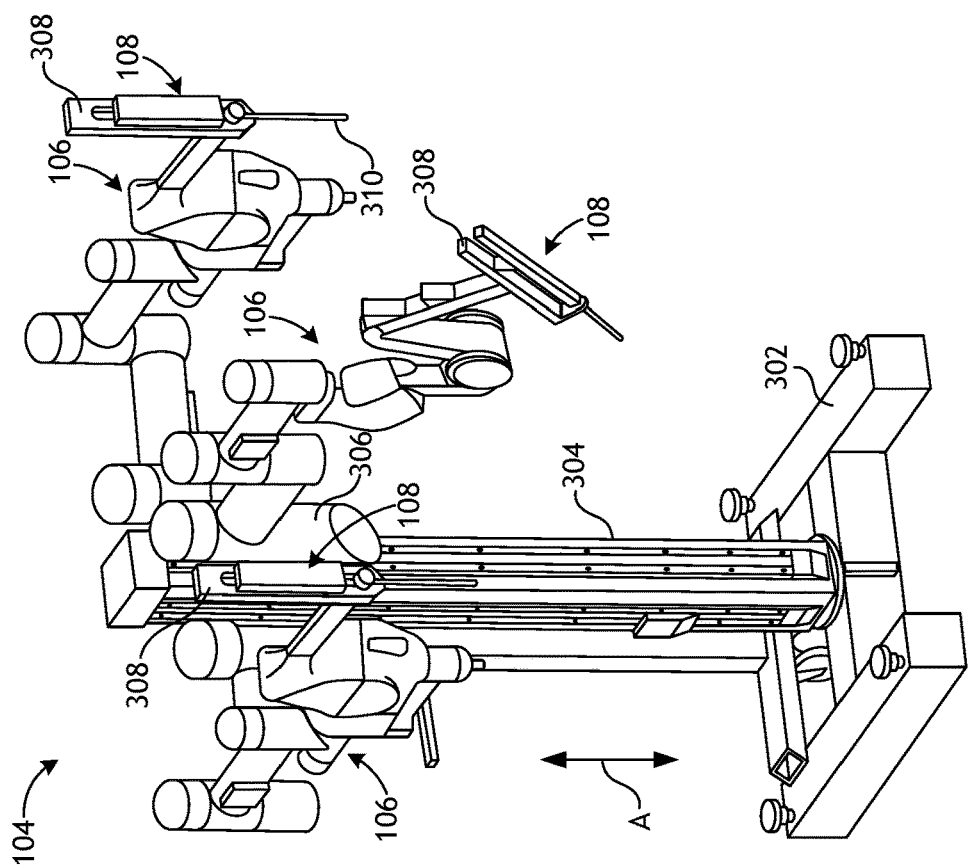
FIG. 3 depicts one example of the robotic manipulator of FIG. 1, according to one or more embodiments.
Figure 2:
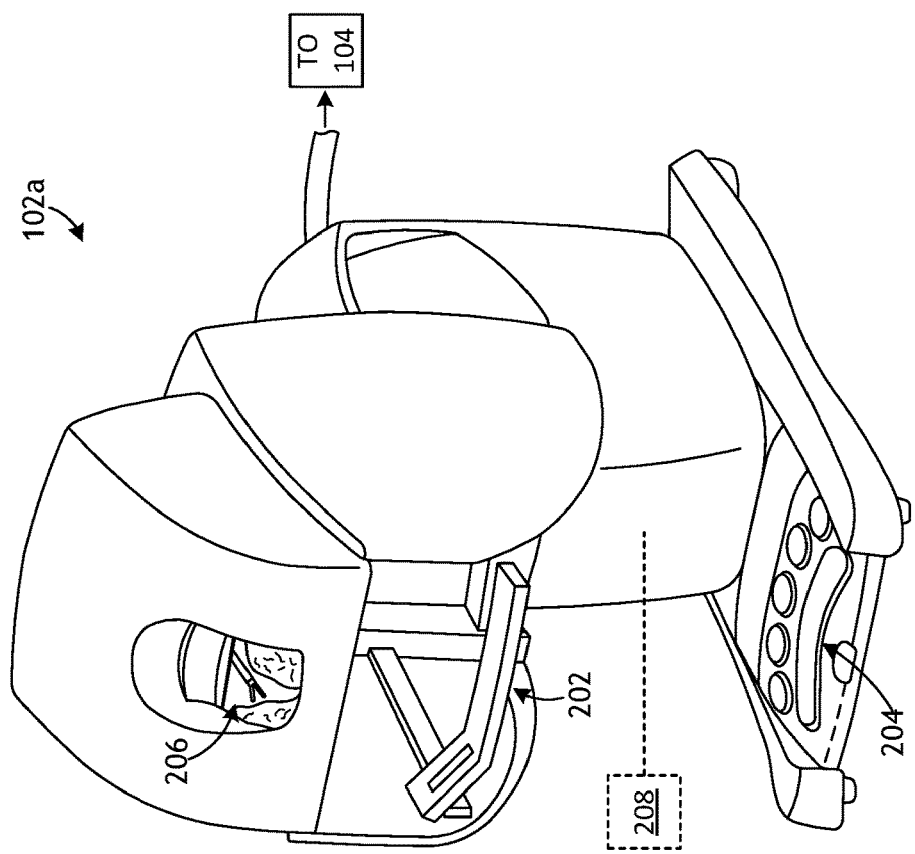
FIG. 2 is an example embodiment of one of the master control consoles of FIG. 1.

FIGS. 1-3 illustrate the structure and operation of an example robotic surgical system and associated components thereof. While applicable to robotic surgical systems, it is noted that the principles of the present disclosure may equally or alternatively be applied to non-robotic surgical systems, without departing from the scope of the disclosure.

FIG. 1 is a block diagram of an example robotic surgical system 100 that may incorporate some or all of the principles of the present disclosure. As illustrated, the system 100 can include at least one master control console 102a and at least one robotic manipulator 104. The robotic manipulator 104 may be mechanically and/or electrically coupled to or otherwise include one or more robotic arms 106. In some embodiments, the robotic manipulator 104 may be mounted to a transport cart (alternately referred to as an "arm cart") that enables mobility of the robotic manipulator 104 and the associated robotic arms 106. Each robotic arm 106 may include and otherwise provide a tool driver where one or more surgical instruments or tools 108 may be mounted for performing various surgical tasks on a patient 110. Operation of the robotic arms 106, the corresponding tool drivers, and the associated tools 108 may be directed by a clinician 112a (e.g., a surgeon) from the master control console 102a.

In some embodiments, a second master control console 102b (shown in dashed lines) operated by a second clinician 112b may also help direct operation of the robotic arms 106 and tools 108 in conjunction with the first clinician 112a. In such embodiments, for example, each clinician 102a,b may control different robotic arms 106 or, in some cases, complete control of the robotic arms 106 may be passed between the clinicians 102a,b. In some embodiments, additional robotic manipulators having additional robotic arms may be utilized during surgery on a patient 110, and these additional robotic arms may be controlled by one or more of the master control consoles 102a,b.

The robotic manipulator 104 and the master control consoles 102a,b may communicate with one another via a communications link 114, which may be any type of wired or wireless communications link configured to carry suitable types of signals (e.g., electrical, optical, infrared, etc.) according to any communications protocol. In some applications, for example, the robotic manipulator 104 may include a tower with ancillary equipment and processing cores designed to drive the robotic arms 106. The communications link 114 may be an actual physical link or it may be a logical link that uses one or more actual physical links. When the link is a logical link the type of physical link may be a data link, uplink, downlink, fiber optic link, point-to-point link, for example, as is well known in the computer networking art to refer to the communications facilities that connect nodes of a network. Accordingly, the clinicians 112a,b may be able to remotely control the robotic arms 106 via the communications link 114, thus enabling the clinicians 112a,b to operate on the patient 110 from remote locations.

FIG. 2 is one example embodiment of the master control console 102a that may be used to control operation of the robotic manipulator 104 of FIG. 1. As illustrated, the master control console 102a can include a support 202 on which the clinician 112a,b (FIG. 1) can rest his/her forearms while gripping two user input devices (not shown), one in each hand. The user input devices can comprise, for example, physical controllers such as, but not limited to, a joystick, exoskeletal gloves, a master manipulator, etc., and may be movable in multiple degrees of freedom to control the position and operation of the surgical tool(s) 108 (FIG. 1). In some embodiments, the master control console 102a may further include one or more foot pedals 204 engageable by the clinician 112a,b to change the configuration of the surgical system and/or generate additional control signals to control operation of the surgical tool(s) 108.

The user input devices and/or the foot pedals 204 may be manipulated while the clinician 112a,b (FIG. 1) views the procedure via a visual display 206. Images displayed on the visual display 206 may be obtained from an endoscopic camera or "endoscope." In some embodiments, and as described in more detail herein, the visual display 206 may include or otherwise incorporate a force feedback meter or "force indicator" that provides the clinician 112a,b with a visual indication of the magnitude of force being assumed by the surgical tool (i.e., a cutting instrument or dynamic clamping member) and in which direction. As will be appreciated, other sensor arrangements may be employed to provide the master control console 102a with an indication of other surgical tool metrics, such as whether a staple cartridge has been loaded into an end effector or whether an anvil has been moved to a closed position prior to firing, for example.

The master control console 102a may further include or otherwise communicate with a computer system 208 that may help control operation of the robotic manipulator 104 (FIG. 1) and the master control console 102a, including the visual display 206. The embodiments described herein may be implemented, at least in part, using the computer system 208, which may be characterized as a digital data processing and programmable system. The computer system 208 may include one or more processors operable to control operation of the computer system 208, and may further include one or more memories that provide temporary storage for code to be executed by the processor(s) or for data acquired from one or more sensors, storage devices, and/or databases.

FIG. 3 depicts one example of the robotic manipulator 104 that may be used to operate a plurality of surgical tools 108, according to one or more embodiments. As illustrated, the robotic manipulator 104 may include a base 302 that supports a vertically extending column 304. A plurality of robotic arms 106 (three shown) may be operatively coupled to the column 304 at a carriage 306 that can be selectively adjusted to vary the height of the robotic arms 106 relative to the base 302, as indicated by the arrow A.

The robotic arms 106 may comprise manually articulable linkages, alternately referred to as "set-up joints." In the illustrated embodiment, a surgical tool 108 is mounted to corresponding tool drivers 308 provided on each robotic arm 106. Each tool driver 308 may include one or more drivers or motors used to interact with a corresponding one or more drive inputs of the surgical tools 108, and actuation of the drive inputs causes the associated surgical tool 108 to operate.

One of the surgical tools 108 may comprise an image capture device 310, such as an endoscope, which may include, for example, a laparoscope, an arthroscope, a hysteroscope, or may alternatively include some other imaging modality, such as ultrasound, infrared, fluoroscopy, magnetic resonance imaging, or the like. The image capture device 310 has a viewing end located at the distal end of an elongate shaft, which permits the viewing end to be inserted through an entry port into an internal surgical site of a patient's body. The image capture device 310 may be communicably coupled to the visual display 206 (FIG. 2) and capable of transmitting images in real-time to be displayed on the visual display 206.

The remaining surgical tools may be communicably coupled to the user input devices held by the clinician 112a,b (FIG. 1) at the master control console 102a (FIG. 2). Movement of the robotic arms 106 and associated surgical tools 108 may be controlled by the clinician 112a,b manipulating the user input devices. As described in more detail below, the surgical tools 108 may include or otherwise incorporate an end effector mounted on a corresponding articulable wrist pivotally mounted on a distal end of an associated elongate shaft. The elongate shaft permits the end effector to be inserted through entry ports into the internal surgical site of a patient's body, and the user input devices also control movement (actuation) of the end effector.

In use, the robotic manipulator 104 is positioned close to a patient requiring surgery and is then normally caused to remain stationary until a surgical procedure to be performed has been completed. The robotic manipulator 104 typically has wheels or castors to render it mobile. The lateral and vertical positioning of the robotic arms 106 may be set by the clinician 112a,b (FIG. 1) to facilitate passing the elongate shafts of the surgical tools 108 and the image capture device 310 through the entry ports to desired positions relative to the surgical site. When the surgical tools 108 and image capture device 310 are so positioned, the robotic arms 106 and carriage 306 can be locked in position.

Figure 4:
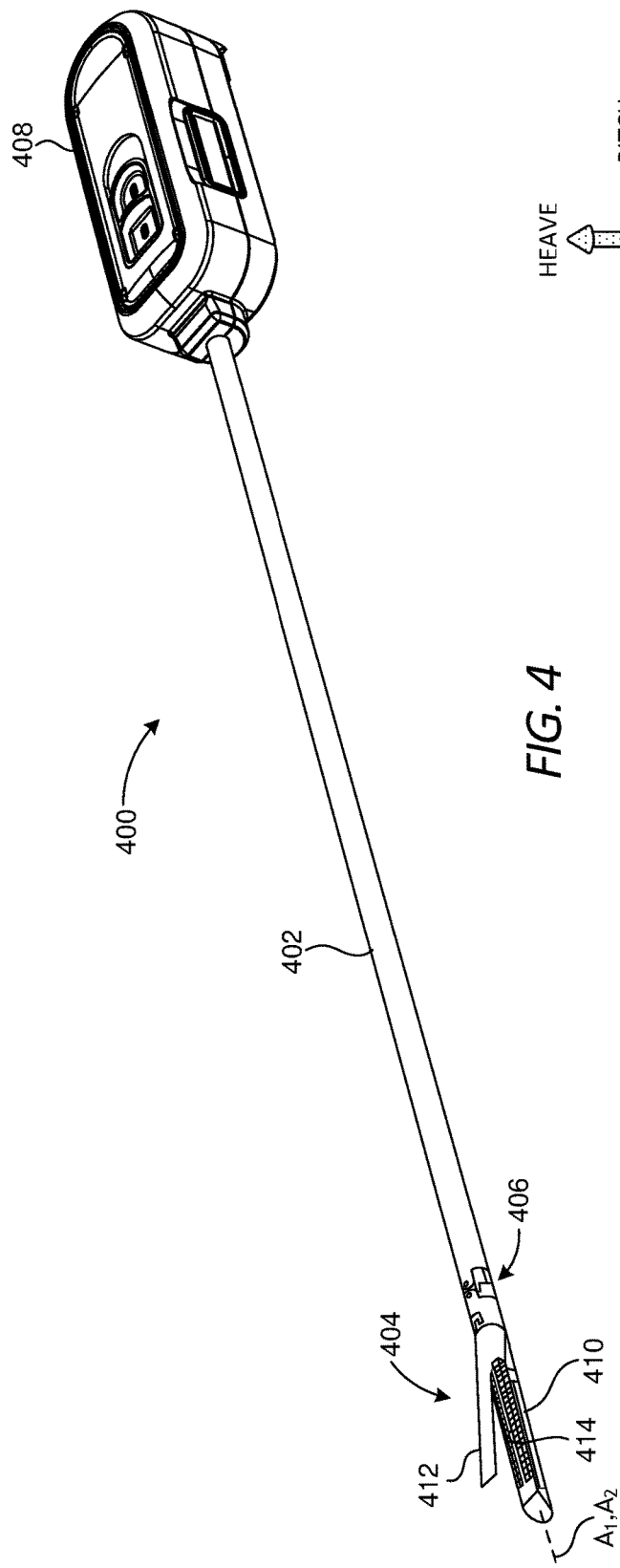
FIG. 4 is a side view of an example surgical tool that may incorporate some or all of the principles of the present disclosure.

FIG. 4 is side view of an example surgical tool 400 that may incorporate some or all of the principles of the present disclosure. The surgical tool 400 may be the same as or similar to the surgical tool(s) 108 of FIGS. 1 and 3 and, therefore, may be used in conjunction with a robotic surgical system, such as the robotic surgical system 100 of FIG. 1. As illustrated, the surgical tool 400 includes an elongated shaft 402, an end effector 404, an articulable wrist 406 (alternately referred to as a "wrist joint") that couples the end effector 404 to the distal end of the shaft 402, and a drive housing 408 coupled to the proximal end of the shaft 402. In applications where the surgical tool 400 is used in conjunction with a robotic surgical system, the drive housing 408 can include coupling features that releasably couple the surgical tool 400 to the robotic surgical system. It will be appreciated, however, that the principles of the present disclosure are equally applicable to surgical tools that are non-robotic and otherwise capable of manual manipulation.

The terms "proximal" and "distal" are defined herein relative to a robotic surgical system having an interface configured to mechanically and electrically couple the surgical tool 400 (e.g., the drive housing 408) to a robotic manipulator. The term "proximal" refers to the position of an element closer to the robotic manipulator and the term "distal" refers to the position of an element closer to the end effector 404 and thus further away from the robotic manipulator. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

The surgical tool 400 can have any of a variety of configurations capable of performing one or more surgical functions. For example, the surgical tool 400 may include, but is not limited to, forceps, a grasper, a needle driver, scissors, an electro cautery tool, a stapler, a vessel sealer, a clip applier, a hook, a spatula, a suction tool, an irrigation tool, an image capture device (e.g., endoscope, ultrasonic probe, etc.), or any combination thereof. In some embodiments, the surgical tool 400 may be configured to apply energy to tissue, such as monopolar energy, radio frequency (RF) energy, or ultrasonic energy.

Figure 5:
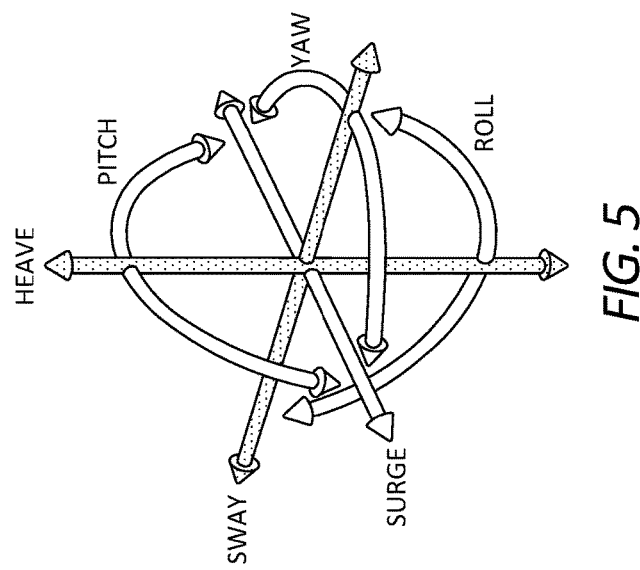
FIG. 5 illustrates potential degrees of freedom in which the wrist of FIG. 4 may be able to articulate (pivot).

In the illustrated embodiment, the wrist 406 enables the end effector 404 to move (pivot) relative to the shaft 402 and thereby position the end effector 404 at desired orientations and locations relative to a surgical site. FIG. 5 illustrates the potential degrees of freedom in which the wrist 406 may be able to articulate (pivot). The wrist 406 can have any of a variety of configurations. In general, the wrist 406 comprises a joint configured to allow pivoting movement of the end effector 404 relative to the shaft 402. The degrees of freedom of the wrist 406 are represented by three translational variables (i.e., surge, heave, and sway), and by three rotational variables (i.e., Euler angles or roll, pitch, and yaw). The translational and rotational variables describe the position and orientation of a component of a surgical system (e.g., the end effector 404) with respect to a given reference Cartesian frame. As depicted in FIG. 5, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 406 (e.g., X-axis), yaw movement about a second axis of the wrist 406 (e.g., Y-axis), and combinations thereof to allow for 360° rotational movement of the end effector 404 about the wrist 406. In other applications, the pivoting motion can be limited to movement in a single plane, e.g., only pitch movement about the first axis of the wrist 406 or only yaw movement about the second axis of the wrist 406, such that the end effector 404 moves only in a single plane.

Referring again to FIG. 4, the shaft 402 extends distally from the drive housing 408 and has at least one lumen extending therethrough along its axial length. In some embodiments, the shaft 402 may be fixed to the drive housing 408, but could alternatively be rotatably mounted to the drive housing 408. In at least one embodiment, the shaft 402 (and hence the end effector 404 coupled thereto) may be configured to rotate about a longitudinal axis $A_1$ of the shaft 402. In such embodiments, at least one drive input included in the drive housing 408 may be configured to control rotational movement of the shaft 402 about the longitudinal axis $A_1$. In yet other embodiments, the shaft 402 may be releasably coupled to the drive housing 408, which may allow a single housing 408 to be adaptable to various shafts having different end effectors.

The end effector 404 can have a variety of sizes, shapes, and configurations. In the illustrated embodiment, the end effector 404 comprises a surgical stapler configured to cut and staple (fasten) tissue. As illustrated, the end effector 404 includes opposing jaws 410, 412 configured to move (articulate) between open and closed positions. As will be appreciated, however, the opposing jaws 410, 412 may alternatively form part of other types of end effectors such as, but not limited to, a tissue grasper, surgical scissors, an advanced energy vessel sealer, a clip applier, a needle driver, a babcock including a pair of opposed grasping jaws, bipolar jaws (e.g., bipolar Maryland grasper, forceps, a fenestrated grasper, etc.), etc. One or both of the jaws 410, 412 may be configured to pivot to articulate the end effector 404 between the open and closed positions. It is noted, however, that the principles of the present disclosure are equally applicable to an end effector that does not include opposing jaws.

In the illustrated embodiment, the first jaw 410 may be characterized or otherwise referred to as a "cartridge" jaw, and the second jaw 412 may be characterized or otherwise referred to as an "anvil" jaw. More specifically, the first jaw 410 may include a frame that houses or supports a staple cartridge, and the second jaw 412 is pivotally supported relative to the first jaw 410 and defines a surface that operates as an anvil to form staples ejected from the staple cartridge during operation. In use, the second jaw 412 is rotatable between an open, unclamped position and a closed, clamped position. In other embodiments, however, the first jaw 410 may move (rotate) relative to the second jaw 412, without departing from the scope of the disclosure.

The surgical tool 400 may also include a plurality of drive members (obscured in FIG. 4) that form part of an actuation system configured to facilitate articulation of the wrist 406 and actuation (operation) of the end effector 404 (e.g., clamping, firing, rotation, articulation, energy delivery, etc.). More specifically, the drive housing 408 may include (contains) various drive inputs and mechanisms (e.g., gears, actuators, etc.), and each drive member is operatively coupled to one or more drive inputs and extend distally from the drive housing 408. Actuation of the drive inputs facilitates longitudinal movement (translation) of the drive members within the shaft 402, which causes the wrist 406 to articulate the end effector 404 to actuate. The drive members may comprise any flexible or rigid elongate member including, but not limited to, a cable, a push cable, a band (e.g., a ribbon), a line, a cord, a wire, a rope, a string, a twisted string, a rod or a shaft (e.g., a hypotube, a hollow rod, a solid rod, etc.), a ribbon, or any combination thereof.

Some drive members may extend to the wrist 406, and selective actuation of these drive members causes the end effector 404 to articulate (pivot) relative to the shaft 402 at the wrist 406. The end effector 404 is depicted in FIG. 4 in the unarticulated position where a longitudinal axis $A_2$ of the end effector 404 is substantially aligned with the longitudinal axis $A_1$ of the shaft 402, such that the end effector 404 is at a substantially zero angle relative to the shaft 402. Due to factors such as manufacturing tolerance and precision of measurement devices, the end effector 404 may not be at a precise zero angle relative to the shaft 402 in the unarticulated position, but nevertheless be considered "substantially aligned" thereto. In the articulated position, the longitudinal axes $A_1$, $A_2$ would be angularly offset from each other such that the end effector 404 is at a non-zero angle relative to the shaft 402.

Other drive members may extend to the end effector 404, and selective actuation of those drive members may cause the end effector 404 to actuate (operate). In the illustrated embodiment, actuating the end effector 404 may comprise closing and/or opening the second jaw 412 relative to the first jaw 410 (or vice versa), thereby enabling the end effector 404 to grasp onto tissue. In addition, once tissue is grasped or clamped between the opposing jaws 410, 412 at a desired location, actuating the end effector 404 may further comprise "firing" the end effector 404. Firing the end effector 404 may generally refer to actuation of the end effector 404. In the depicted embodiment, firing the end effector 404 may refer to causing a cutting element (not visible) to advance distally within a slot 414 defined in the second jaw 410 while the second jaw 412 is clamped down, and the cutting element may transect the tissue grasped between the opposing jaws 410, 412 as it moves distally. As the cutting element advances distally, a plurality of staples contained within the staple cartridge (i.e., housed within the first jaw 410) may be urged (cammed) into deforming contact with corresponding anvil surfaces (e.g., pockets) provided on the second jaw 412. The deployed staples may form multiple rows of staples that seal opposing sides of the transected tissue. In the case of an energy device, firing the end effector 404 may generally refer to the application of energy to tissue grasped or clamped between two opposing jaws to cauterize or seal the captured tissue, following which the tissue may be transected.

Excessive and uneven tension in the grasped tissue during staple formation can negatively affect formation of the staples. More specifically, if there is excessive tension in the grasped tissue, the staples penetrating the tissue during firing may become misguided (misdirected) toward the corresponding anvil surfaces (e.g., pockets) provided on the second jaw 412, thereby resulting in improperly bent (formed) staples. Ideally, tension in the tissue during firing of the end effector 404 is at or near zero so that the only thing driving staple formation is the perpendicular camming force that urges the staples toward the anvil surfaces of the second jaw 412. With other types of end effectors, however, elevated tissue tension, or tissue tension delivered in a particular direction may be desired.

The presently disclosed systems and methods are directed to managing and optimizing tissue tension without adversely affecting surrounding tissue. In some embodiments, for example, the presently described systems may be configured to reduce tissue tension to at or near zero and simultaneously eliminate any angular tension (torque) on the tissue. In embodiments where the end effector 404 is a surgical stapler, as depicted, the presently described systems may further be configured to create axially directed tension to mitigate the occurrence of the cutting element pushing tissue out of the closed jaws 410, 412 during firing. In other embodiments, however, the presently described systems may be configured to alter tissue tension to a desired (predetermined) tissue tension applied (delivered) in a particular direction. Such embodiments may prove advantageous with an end effector scissors or ultrasonic energy tool that operate more effectively when cutting through tissue in tension.

Figure 6:
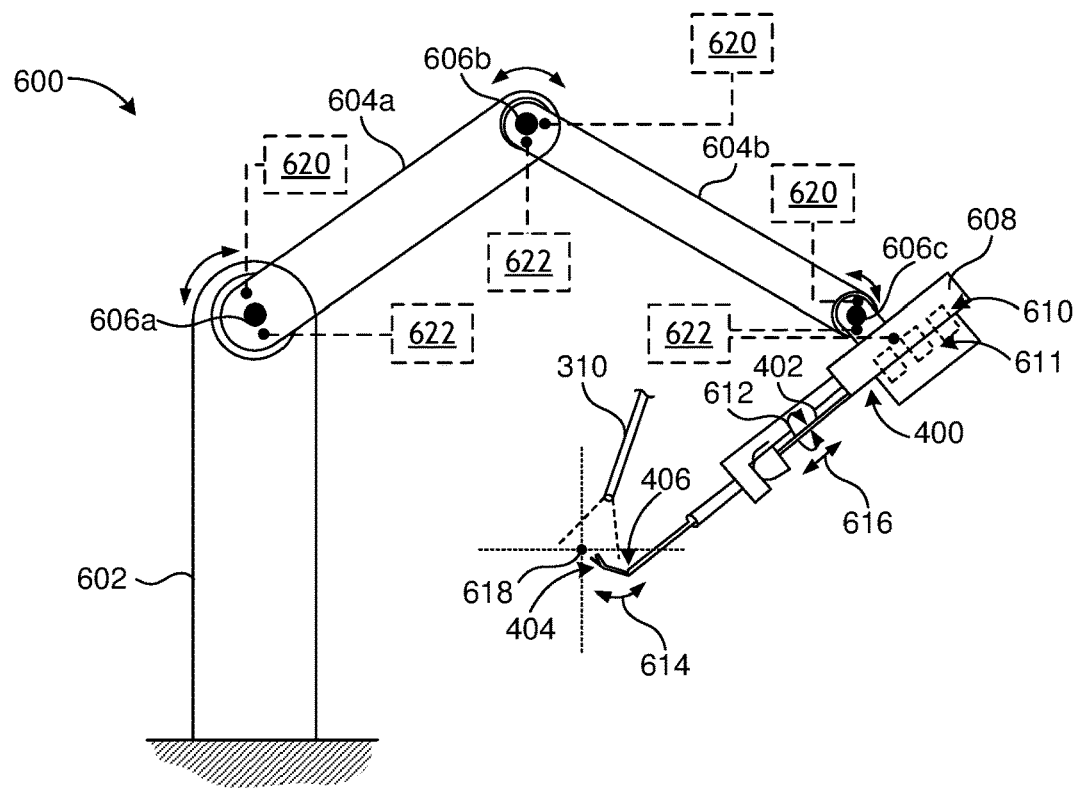
FIG. 6 is a schematic diagram of an example robotic arm that may incorporate one or more principles of the present disclosure.

FIG. 6 is a schematic diagram of an example robotic arm 600 that may incorporate one or more principles of the present disclosure. The robotic arm 600 may be similar in some respects to any of the robotic arms 106 of FIGS. 1 and 3 and, therefore, may be best understood with reference thereto. Moreover, the robotic arm 600 may be used with the robotic manipulator 104 (FIGS. 1 and 3). As illustrated, the robotic arm 600 may include a vertically extending column 602 and a set-up joint extending from the column 602 and comprising a plurality of links or linkages, shown as a first linkage 604a and a second linkage 604b. In at least one embodiment, the column 602 and the interconnected linkages 604a,b may be similar to or the same as the robotic manipulator 104 of FIGS. 1 and 3. The first linkage 604a may be pivotably coupled to the column 602 at a first joint 606a, and the second linkage 604b may be pivotably coupled to the first linkage 604a at a second joint 606b. While two linkages 604a,b are depicted, more than two may be employed in the robotic arm 600, without departing from the scope of the disclosure.

A tool driver 608 (alternately referred to as a "carriage") may be pivotably coupled to the second linkage 604b at a third joint 606c and provide a location where the surgical tool 400 of FIG. 4 may be mounted to the robotic arm 600. As will be appreciated, the surgical tool 400 may be replaced with any other suitable surgical tool, without departing from the scope of the disclosure. The tool driver 608 may include one or more actuators 610 (alternately referred to as "motors" or "drivers") that interact with one or more corresponding drive inputs 611 of the surgical tool 400. Operation of the actuators 610 causes actuation of the associated drive inputs 611, which causes corresponding drive members to move longitudinally within the shaft 402 and thereby rotate the shaft 402 (as indicated at rotational direction 612), articulate the wrist 406 (as indicated at pivot direction 614), and/or actuate (operate) the end effector 404, as generally described above. Moreover, in some embodiments, the tool driver 608 may be configured to move the surgical tool 400 axially relative to the tool driver 608, as indicated by the arrows 616.

Each joint 606a-c may provide a pivotal connection that allows the linkages 604a,b and the tool driver 608 to pivot and move to position the surgical tool 400 and, more particularly, the end effector 404 in desired angular configurations relative to a surgical site 618. Each joint 606a-c may include, for example, one or more actuators 620 that help facilitate pivoting movement of the linkages 604a,b and also provide for force feedback, gravity compensation, and the like. Suitable actuators 620 include, but are not limited to, an electric motor, a servo, a servomechanism, or any combination thereof. The actuators 610, 620 of the tool driver 608 and the joints 606a-c may be in communication (either wired or wirelessly) with the computer system 208 (FIG. 2), which may be programmed to operate the robotic arm 600 and the tool driver 608 and thereby position the surgical tool 400 and, more particularly, the end effector 404 in desired angular configurations relative to the surgical site 618.

An image capture device, such as the image capture device 310 (partially shown), may be arranged to capture images of the surgical site 618 and transmit such images to the computer system 208, which conveys the images to the visual display 206 (FIG. 2) for viewing by the operator (e.g., a surgeon). In use, the operator views the surgical site 618 on the visual display 206, and the end effector 404 is actuated (articulated, operated, etc.) in response to input signals provided by the operator as the operator moves and/or manipulates the user input devices. The computer system 208 with its microprocessors interprets movements and actuation of the user input devices to generate control signals that trigger operation of the actuators 610, 620 and thereby control the robotic arm 600 and the end effector 404. Images of the surgical site 318 and the movement and actuation of the end effector 404 are displayed on the visual display 206 so that the operator sees the responsive movements and actions in real-time.

The robotic arm 600 may further include one or more sensors 622 positioned in each joint 606a-c and in the tool driver 608 to monitor and track motion at each location as the actuators 610, 620 operate. Suitable sensors 622 include, but are not limited to, rotary encoders, linear encoders, potentiometers, accelerometers, torque sensors, force sensors, or any combination thereof. The sensors 622 may also be in communication (either wired or wirelessly) with the computer system 208 (FIG. 2), which may receive position signals from the sensors 622 corresponding to movement of the robotic arm 600 at the joints 606c, rotation 612 of the shaft 402, articulation 614 of the wrist 406, and axial translation 616 of the entire surgical tool 400. Using these positional data points, and based on the mathematical process of inverse kinematics, which takes into account the known geometry of the robotic arm 600 and the surgical tool 400, the computer system 208 may be programmed to aggregate (combine) these signals and thereby determine the movement and real-time (current) position of the end effector 404 relative to the surgical site 618.

In at least one embodiment, the computer system 208 (FIG. 2) may be programmed and otherwise configured to counteract inadvertent movement (jostling) of the robotic arm 600 that would correspondingly affect the position of the end effector 404. More specifically, while rare, unintentional contact with the robotic arm 600 during an operation can occur, such as when medical personnel accidentally bump into the robotic arm 600. In such instances, the position of the end effector 404 will be moved (jostled) in the same direction, which could result in damage to tissue or other bodily structures. Since the real-time position of the end effector 404 is known, any inadvertent movement of the robotic arm 606 can be countered by opposing movement provided by the robotic arm 606 and/or movement of the surgical tool 400. In some embodiments, for example, the angle of one or more of the joints 606a-c may be adjusted to counteract inadvertent movement of the robotic arm 606, thus minimizing or neutralizing movement at the end effector 404. In other embodiments, the shaft 402 may be rotated 612, the wrist 406 may be articulated 614, the second jaw 412 may be actuated, and/or the entire surgical tool 400 may be axially translated 616 to minimize or neutralize movement at the end effector 404. In yet other embodiments, a combination of actuation provided by the robotic arm 606 and the surgical tool 400 may be employed to minimize or neutralize movement of the end effector 404. As will be appreciated, such force divergence measures may be undertaken autonomously using the computer system 208 (FIG. 2).

According to embodiments of the present disclosure, the sensors 622 may also provide real-time loading data (force, torque, pressure, direction of force, etc.) to the computer system 208 (FIG. 2), which may allow the computer system 208 to calculate real-time loading on the end effector 404. More specifically, since all the actuators 610, 620 cooperatively support movement and position of the end effector 404, all loading on the end effector 404 is reacted through one or more of the actuators 610, 620. The computer system 208 may be programmed to aggregate (combine) the loading data obtained from the sensors 622 and, through inverse kinematics which takes into account the known geometry of the robotic arm 600 and the surgical tool 400, determine the angle of the loading (e.g., a force vector) on the end effector 404. Example methods of performing inverse kinematics include, but are not limited to, Jacobian inverse and heuristic methods. Accordingly, when the end effector 404 grasps tissue during operation or otherwise engages a bodily structure, the data provided by the sensors 622 may allow calculation of the magnitude and direction of loading on the end effector 404, thus resulting in the calculation of a force vector assumed by the end effector 404. In a scenario where the end effector 404 grasps tissue, the calculated force vector may be representative of the force experienced by the grasped tissue.

Figure 7:
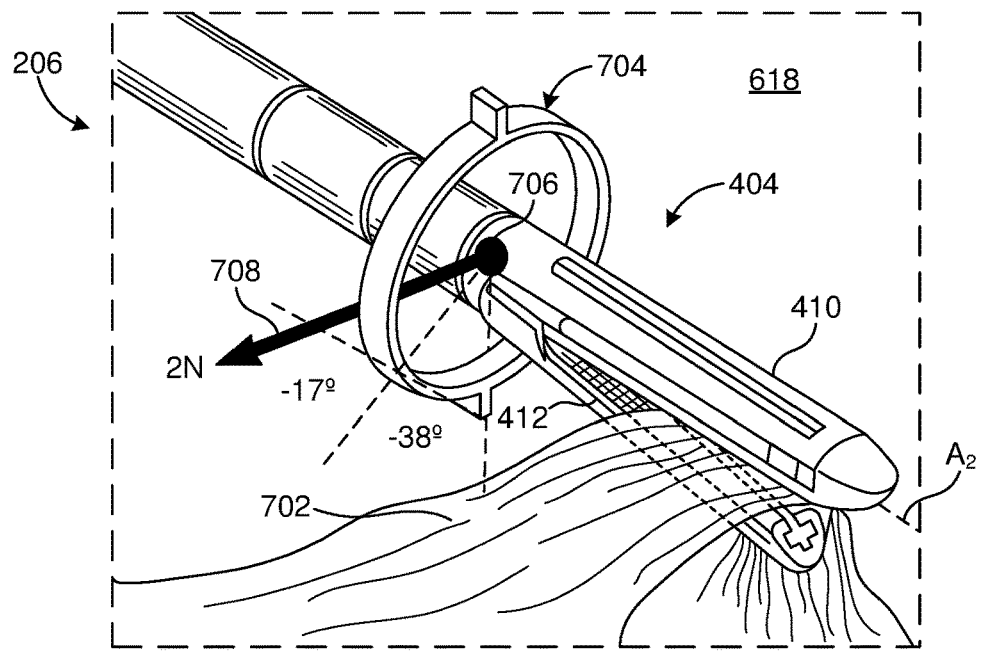
FIG. 7 is an example graphical output of the visual display of FIG. 2, according to one or more embodiments.

Referring now to FIG. 7, with continued reference to FIG. 6, illustrated is an example graphical output of the visual display 206, according to one or more embodiments. More specifically, FIG. 7 depicts a graphical representation of the surgical site 618 as obtained (captured) by the image capture device 310. As illustrated, a portion of tissue 702 is grasped between the opposing jaws 410, 412 of the end effector 404.

According to embodiments of the present disclosure, the computer system 208 (FIG. 2) may be programmed to augment the visual display 206 with a computer-generated force indicator 704 that graphically provides the magnitude and direction of loading assumed by the end effector 404 in real-time. In the illustrated embodiment, the force indicator 704 is displayed as a three-dimensional (3D) ring (e.g., an orientation ring) that extends about the end effector 404 generally perpendicular to the longitudinal axis $A_2$ of the end effector 404. In other embodiments, however, the force indicator 704 may be displayed in any other suitable form or geometry (e.g., polygonal, ovoid, etc.), or in any other configuration sufficient to convey real-time loading assumed by the end effector 404. In other embodiments, for example, the force indicator 704 may be displayed as Cartesian axes extending through a known location on the end effector 404.

As illustrated, the force indicator 704 may be graphically tied (coupled) to the end effector 404 at a known reference point 706 relative to the end effector 404. The location of the reference point 706 may be determined based on the known geometry of the robotic arm 600 and the surgical tool 400. In the illustrated embodiment, the reference point 706 is located at or near the pivot point between the opposing jaws 410, 412. In other embodiments, however, the reference point 706 may be located at other locations, such as at or near the distal tip of the end effector 404, without departing from the scope of the disclosure.

The force indicator 704 may provide or otherwise include a computer-generated, graphically displayed force vector 708 extending from the reference point 706 and indicating the real-time magnitude and direction of the forces (loading) assumed on the end effector 404. The magnitude and direction of the force vector 708 may be determined by the computer system 208 (FIG. 2) based on data obtained by the sensors 622 and using inverse kinematics, which takes into account the known geometry of the robotic arm 600 and the surgical tool 400. In the illustrated example, the force vector 708 indicates that a 2 Newton (N) force is assumed by the end effector 404 in the indicated direction and is representative of the tension in the grasped tissue 702, i.e., tissue tension.

Figure 8A:
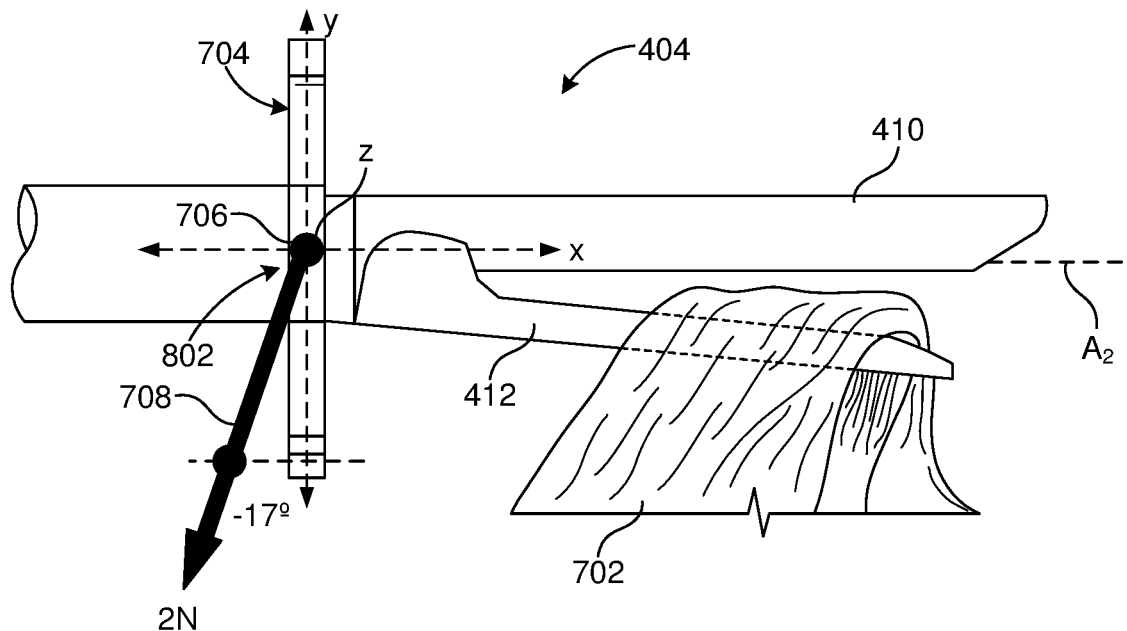
FIGS. 8A and 8B depict side and end views, respectively, of the end effector of FIG. 7 grasping tissue between its jaws.
Figure 8B:
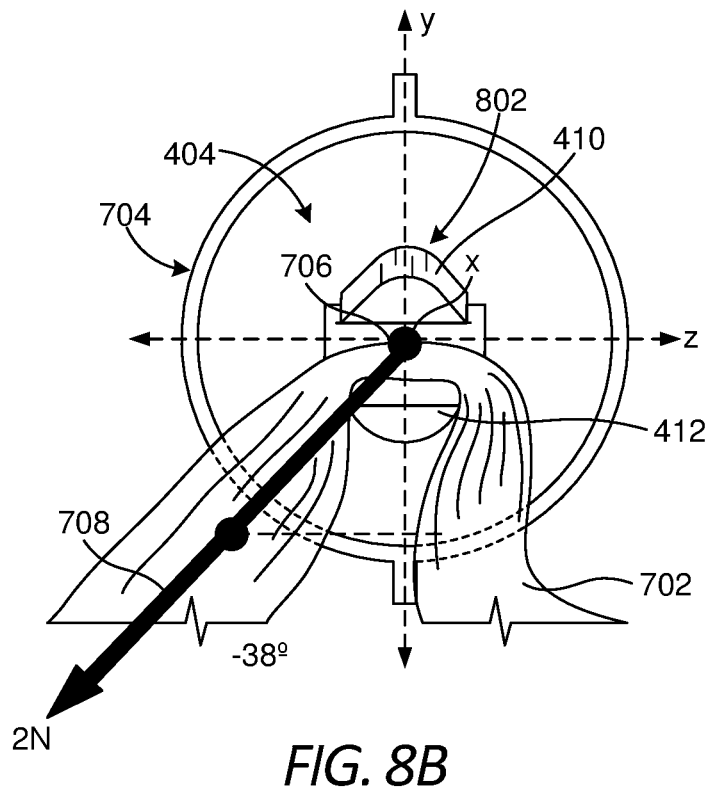

Referring briefly to FIGS. 8A and 8B, depicted are side and end views, respectively, of the end effector 404 grasping the tissue 702 between its jaws 410, 412. Also illustrated is the computer-generated force indicator 704 and an associated Cartesian coordinate system 802 aligned with the force indicator 704. The Cartesian coordinate system 802 is depicted to show how the force vector 708 is calculated and graphically displayed, and includes x-, y-, and z-axes that meet at the reference point 706. In the illustrated embodiment, the x-axis runs parallel to the longitudinal axis $A_2$ of the end effector 404, the y-axis is perpendicular to the x-axis and parallel to the ring structure of the force indicator 704, and the z-axis is perpendicular to both the x- and y-axes.

Based on the real-time loading data provided by the sensors 622 (FIG. 6) to the computer system 208 (FIG. 2), and using known techniques of assigning vector coordinates in three dimensions, the magnitude and direction of the force vector 708 originating at the reference point 706 may be determined and graphically displayed with reference to the Cartesian coordinate system 802. In FIGS. 8A-8B, for example, the force vector 708 may be calculated to pass through coordinates x=−0.2, y=−0.4, and z=−0.35, which corresponds to the force vector 708 extending at −17° between the y- and x-axes, as shown in FIG. 8A, and extending at −38° between the y- and z-axes, as shown in FIG. 8B. The resulting force vector 708 comprises a combination of these values.

In some embodiments, FIGS. 8A-8B may comprise computer-generated views or displays available to the operator (surgeon) to help the operator better determine the specific direction of the force vector 708. More particularly, the view of the surgical site 618 in FIG. 7 may be referred to as a "scope view" obtained through images captured by the image capture device 310 (FIG. 6). The images displayed in FIGS. 8A-8B, however, may be referred to as "side" and "end" views, respectively, or "custom views" comprising 3D models of the surgical site 618 generated by the computer system 208 (FIG. 2). As discussed in more detail below, in some cases, the scope view might not clearly indicate the load direction for the force vector 708 as a result of the angle of image capture, thus leaving the operator with an ambiguous view of the direction and magnitude of the force vector 708. In such cases, the operator may have the option of creating alternate graphical representations of the surgical site 618 with the computer system 208, such as those seen in FIGS. 8A-8B. As will be appreciated, these alternate views may prove advantageous in allowing the operator to better judge where the current force vector 708 lies and its true direction.

Referring again to FIG. 7, with continued reference to FIG. 6, as the end effector 404 is moved in space during operation and/or to adjust the position of the end effector 404, the computer system 208 (FIG. 2) may be programmed to correspondingly alter the graphical position of the force indicator 704 and thereby maintain the force indicator 704 centered at the reference point 706. Moreover, the computer system 208 may be programmed to continuously update the direction and magnitude of the force vector 708 while the end effector 404 operates or moves, thus providing the operator (surgeon) with the real-time magnitude and direction of the forces assumed on the end effector 404.

With the measured force vector 708 graphically displayed on the visual display 206 in real-time, the operator (surgeon) may then make an informed decision whether to proceed with firing (actuating) the end effector 404 (e.g., transecting and stapling the tissue 702), or whether it may be advisable to optimize the magnitude and/or direction of the force vector 708 before proceeding. For example, the operator may decide to correct or otherwise reduce the magnitude of the force vector 708, thus mitigating the potential for improperly bent (formed) staples. As described herein, optimizing the force vector 708 may be done manually, semi-automatically, or automatically, and the operator may have the ability to select which methodology to employ.

Figure 9C:
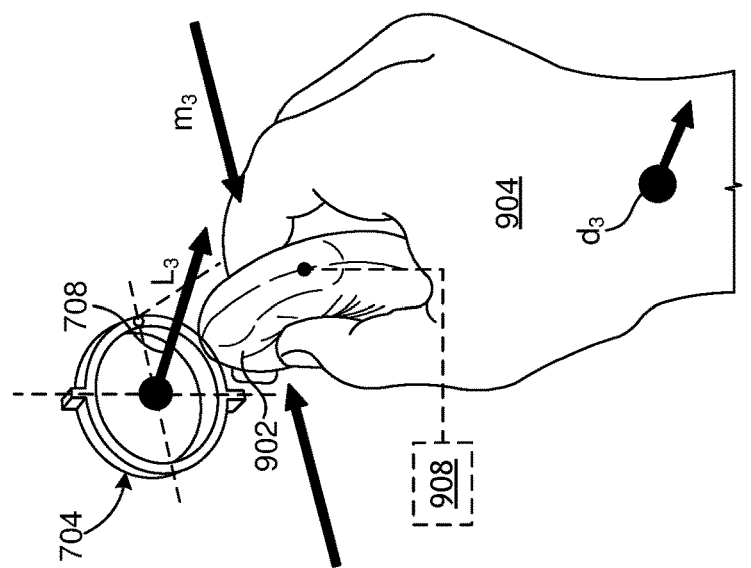
FIGS. 9A-9C are graphical representations of an operator optimizing the force vector of FIG. 7, according to one or more embodiments.
Figure 9B:
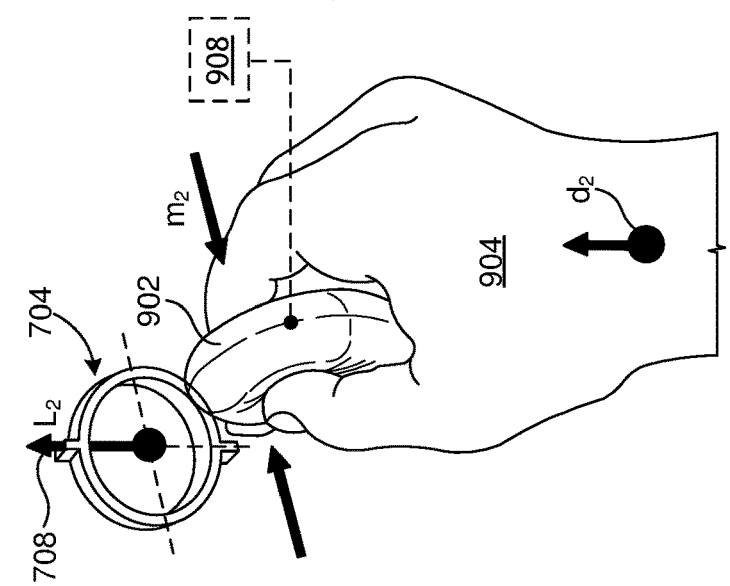
Figure 9A:
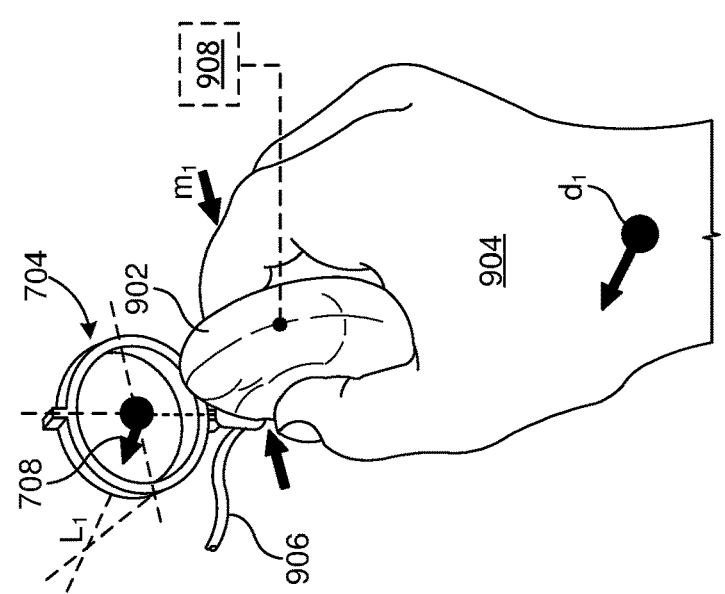

FIGS. 9A-9C are graphical representations of an operator optimizing the force vector 708, according to one or more embodiments. More specifically, illustrated is a user input device 902 grasped by the right hand 904 of the operator, and manipulation of the user input device 902 may alter the magnitude and direction of the force vector 708 provided by the force indicator 704. In some embodiments, the user input device 902 may communicate with the computer system 208 (FIG. 2) via wired communication 906 (FIG. 9A), but may alternatively communicate via any suitable wireless modality, without departing from the scope of the disclosure.

The user input device 902 may include multiple sensors and/or gauges 908 (e.g., pressure sensors, accelerometers, position tracking devices, electric or mechanical switches, etc.) used to measure force (e.g., pressure) applied by the operator and track direction (location) of the user input device 902 as the hand 904 moves the user input device 902 in 3D space. Signals obtained by the sensors 908 may be conveyed to the computer system 208 (FIG. 2), which may be programmed to convert the signals into corresponding movement of the end effector 404, which may correspondingly optimize the force vector 708 to a desired magnitude and direction. More particularly, the magnitude of the squeeze on the user input device 902 in combination with the directional movement of the hand 904 will dictate the magnitude and direction of the force vector 708 applied at the end effector 404 (FIG. 7).

In FIG. 9A, the operator provides a light squeeze on the user input device 902 to a magnitude of $m_1$, and simultaneously moves the hand 904 in a first direction $d_1$, which results in a measured force vector 708 of $L_1$ at the force indicator 704. In FIG. 9B, the operator provides a medium squeeze (i.e., greater than the light squeeze) on the user input device 902 to a magnitude of $m_2$, and simultaneously moves the hand 904 in a second direction $d_2$, which results in a measured force vector 708 of $L_2$ at the force indicator 704. In FIG. 9C, the operator provides a hard squeeze (i.e., greater than the light and medium squeeze) on the user input device 902 to a magnitude of $m_3$, and simultaneously moves the hand 904 in a third direction $d_3$, which results in a measured force vector 708 of $L_3$ at the force indicator 704.

The force indicator 704 and corresponding force vector 708 may be viewable by the operator (surgeon) in real-time on the visual display 206 (FIGS. 2 and 7), thus providing the operator with immediate visual feedback while manipulating the user input device 902 to the desired force and direction to achieve a particular force vector 708. As will be appreciated, this enables the operator to alter the input signals provided to the user input device 902 and observe in real-time as the graphically-provided force vector 708 changes, thereby obtain a resulting force vector 708 that is more amenable to the operation being undertaken. For example, in some applications, it may be desirable to correct, counteract, or otherwise neutralize a measured force vector 708. To accomplish this, the operator may manipulate (e.g., squeeze, move, etc.) the user input device 902 until achieving the desired optimized force vector 708, which may have minimal or no load.

In some embodiments, the operator may manipulate the user input device 902 and the computer system 208 (FIG. 2) may be programmed to simultaneously operate the robotic arm 606 (FIG. 6) and the surgical tool 400 (FIG. 6) in real-time to alter the force vector 708 assumed on the end effector 404 (FIG. 7). Such embodiments may be referred to herein as "manual mode," which allows the operator to change the measured force vector 708 in real-time.

In other embodiments, however, the operator may manipulate the user input device 902 to program a desired force vector 708 assumed on the end effector 404 (FIG. 7), and the computer system 208 (FIG. 2) may be programmed to operate the robotic arm 606 (FIG. 6) and the surgical tool 400 (FIG. 6) at a subsequent point in time (e.g., at the time of firing) to achieve the desired force vector 708. Such embodiments may be referred to herein as "semi-automatic mode." In the semi-automatic mode, the computer system 208 operates the robotic arm 606 and the surgical tool 400 at a specified time, such as when the end effector 404 clamps down on tissue.

In yet other embodiments, the operator may simply input the desired magnitude and direction for the force vector 708 into the computer system 208 (FIG. 2), such as via a graphical user interface or the like. The computer system 208 may be programmed to operate the robotic arm 606 and the surgical tool 400 to achieve the desired force vector 708 at a subsequent point in time, such as when the end effector 404 clamps down on tissue and/or throughout the firing process. Such embodiments may be referred to herein as "automatic mode." In automatic mode, the computer system 208 may further be programmed to operate the robotic arm 606 and the surgical tool 400 to maintain the desired force vector 708 on the end effector 404 (FIGS. 6 and 7) during operation. In some embodiments carried out in "automatic mode," the magnitude and/or direction of the vector loading may be calculated automatically by the computer system 208 based on machine learning.

Figure 10:
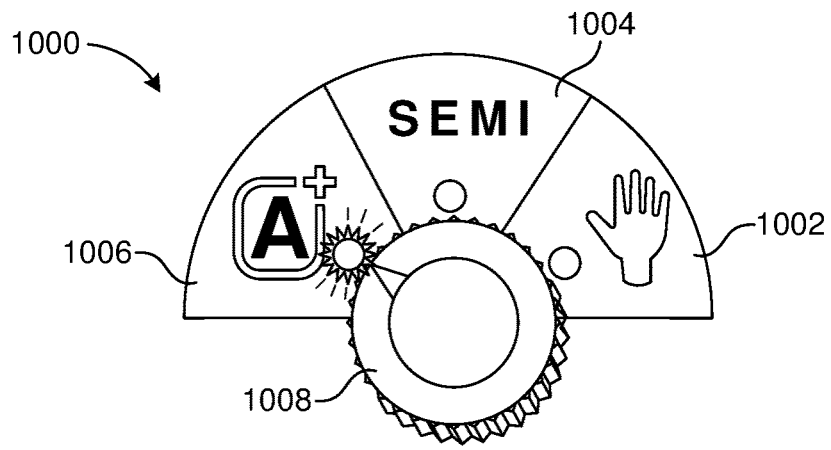
FIG. 10 is a schematic diagram of an example selector that may be used in accordance with the present disclosure.

FIG. 10 is a schematic diagram of an example selector or "dial" 1000 that may be used in accordance with the present disclosure. The selector 1000 may comprise a type of user interface that provides a location or mechanism where the operator may transition the system (e.g., the system 100 of FIG. 1) between manual mode 1002, semi-automatic mode 1004, and automatic mode 1006, as generally described above. In some embodiments, the selector 1000 may form part of the master control console 102a (FIG. 2) and may communicate with the computer system 208 (FIG. 2). In other embodiments, the selector 1000 may be remote from the master control console 102a, but still capable of communication with the computer system 208.

The selector 1000 may comprise any type of user interface capable of allowing the user to selectively switch between the manual, semi-automatic, and automatic modes 1002, 1004, 1006. In the illustrated embodiment, for example, the selector 1000 comprises a rotary dial 1008 manually rotatable (movable) by the operator between the various modes 1002, 1004, 1006. As illustrated, the rotary dial may have an arrow feature that, when pointed to a particular mode, provides an indication of the selected mode. In other embodiments, however, the selector 1000 may comprise another type of mechanical interface, or may alternatively comprise a digital interface where the operator is able to select the desired mode 1002, 1004, 1006 from a graphical user interface or the like.

In some embodiments, as illustrated, the selector 1000 may include an indicator, such as an LED light or the like, that may be triggered when a particular mode is selected to provide the user with a positive indication of the selected mode. Additionally, it is contemplated that the non-selected modes may be dimmed or "blacked-out" to further distinguish the current selected setting from the other settings options available.

Figure 11:
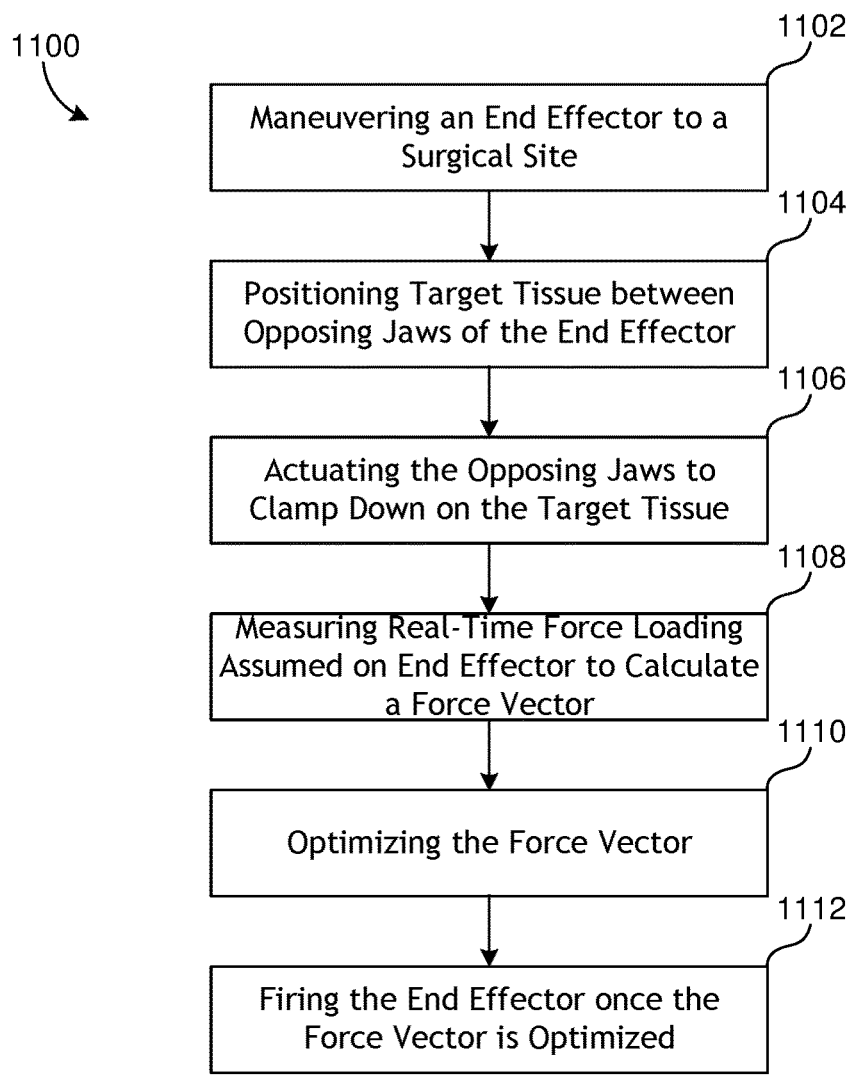
FIG. 11 is a schematic flowchart of an example method of optimizing loading on a surgical tool end effector, according to one or more embodiments.

FIG. 11 is a schematic flowchart of an example method 1100 of optimizing loading on a surgical tool end effector, according to one or more embodiments. The method 1100 may be used, for example, in operating the system shown in FIGS. 6 and 7 and, more particularly, in optimizing the force vector 708 (FIG. 7) assumed by the end effector 404 (FIGS. 6 and 7) of the surgical tool 400 (FIGS. 4 and 6). Accordingly, the following discussion of the method 1100 will reference the parts and features depicted in FIGS. 6 and 7. It will be appreciated, however, that the method 1100 may be used with other systems and surgical tools, without departing from the scope of the disclosure.

According to the method 1100, the end effector 404 may first be maneuvered to a surgical site, as at 1102. The surgical site may be located within a patient's abdomen, and may comprise, for example, the surgical site 618 of FIGS. 6 and 7. In some embodiments, an operator (surgeon) may enter tele-operative mode to maneuver the end effector 404 to the surgical site 618 using user input devices (e.g., the user input device 902 of FIGS. 9A-9C). In such embodiments, the operator may observe the surgical site 618 via the visual display 206 (FIG. 2), which provides images captured by the image capture device 310 (FIG. 6). In other embodiments, a robotic arm, such as the robotic arm 600 of FIG. 6, may direct the end effector 404 to the surgical site 618 under the direction of the computer system 208 (FIG. 2). In yet other embodiments, a combination of operational input by the operator and the computer system 208 may be used to direct the end effector 404 to the surgical site 618.

Once the end effector 404 arrives at the surgical site 618, the operator may enter the tele-operative mode (if not already in such mode) and maneuver the end effector 404 using the user input devices to position target tissue between the opposing jaws 410, 412 of the end effector, as at 1104. The target tissue may comprise, for example, the tissue 702 of FIGS. 7 and 8A-8B, and may otherwise comprise any tissue that requires dissection, sealing, transection, or manipulation using the end effector 404. The operator may view movement of the end effector 404 and the tissue 702 at the surgical site 618 in real-time via the visual display 206.

Once the target tissue 702 is properly positioned therebetween, the opposing jaws 410, 412 may be actuated (operated) to clamp down on the target tissue 702, as at 1106. In some embodiments, clamping down on the target tissue may activate "tension relief mode," which allows the operator to optimize loading forces assumed on the end effector 404 prior to proceeding and/or firing the end effector 404. The tension relief mode can be active when moving the end effector 404 when clamped, when the end effector 404 is clamped and another instrument creates tension on the clamped tissue 702, and/or when the end effector 404 is clamped and the tissue 702 structure itself creates tension in the clamped state.

In the tension relief mode, real-time force loading assumed on the end effector 404 may be measured to calculate a force vector 708 (FIGS. 7, 8A-8B), as at 1108, and as generally described above. In some embodiments, the force vector 708 may be graphically displayed to the operator via the visual display 206 and in conjunction with the force indicator 704 (FIGS. 7, 8A-8B). Accordingly, the visual display 206 may be augmented with the real-time magnitude and direction of the loading on the end effector 404.

The force vector 708 may then be optimized, as at 1110. For example, the operator may proceed in "manual mode" and may optimize the force vector 708 manually while observing the visual display 206, as generally described above. In other embodiments, the operator may proceed in "semi-automatic mode" or "automatic mode" and program the computer system 208 (FIG. 2), either manually or digitally, with a desired magnitude and direction and thereafter allow the computer system 208 to direct the robotic arm 600 and the surgical tool 400 in optimizing the force vector 708, as also generally described above. Once the force vector 708 is optimized, the end effector 404 may then be fired (actuated), as at 1112. Firing the end effector 404 may entail cutting and stapling the target tissue 702. However, firing other types of end effectors may entail other actuation movements.

In some embodiments, the end effector 404 may be prevented from firing (e.g., cutting and stapling the tissue 702) until the force vector 708 is optimized (altered) to a predetermined magnitude or direction. In such applications, the tension relief mode may remain active until the force vector 708 is optimized, and until that point, the firing capability of the surgical tool 400 may be disabled. Accordingly, the tension relief mode may operate as a failsafe that prevents the end effector 404 from transitioning between the clamping and firing states until the force vector 708 is suitably optimized.

In some embodiments, tissue tension monitoring may remain active throughout the firing process. In such embodiments, the computer system 208 (FIG. 2) may be programmed to autonomously maintain the force vector 708 at a predetermined magnitude and/or direction until the firing process is completed. Accordingly, reduction and balancing of the force vector 708 may be done algorithmically by the robotic system during the tension relief mode. In some embodiments, tissue tension monitoring and display of the force indicator 704 (FIGS. 7, 8A-8B) can be turned on/off by the operator manually. In other embodiments, tissue tension monitoring and display of the force indicator 704 may be automatically turned on/off based on the state of the surgical tool 400, such as being activated (turned on) only upon entering the tension relief mode, and turned off following firing of the end effector 404.

Figure 12A:
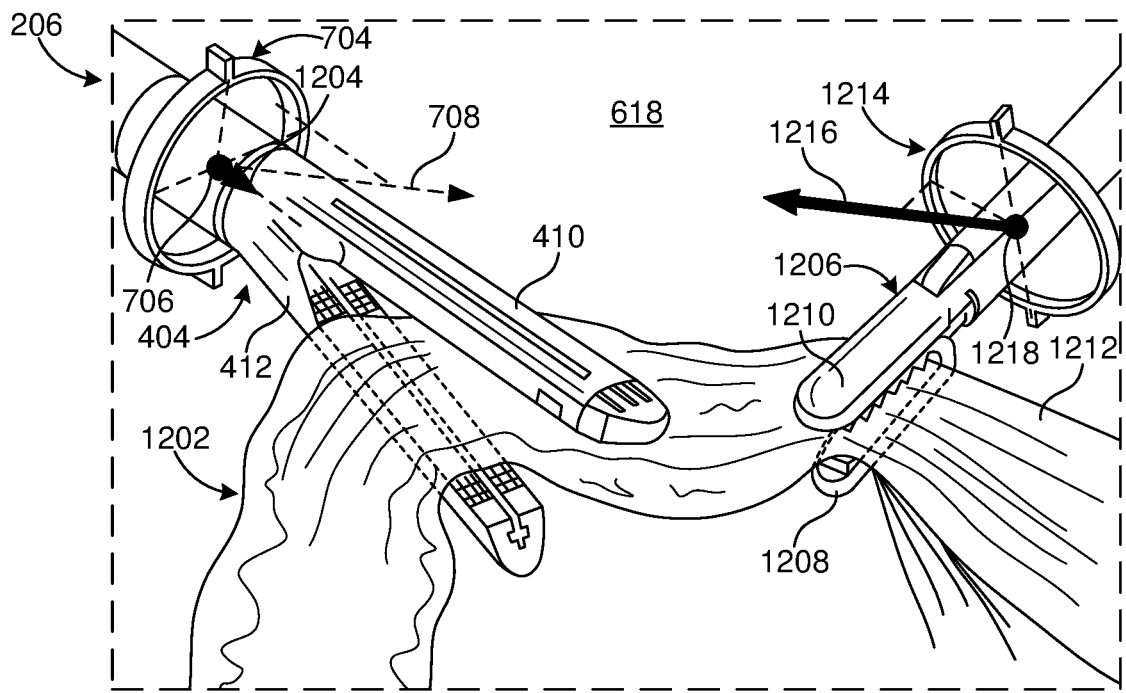
FIG. 12A is another example graphical output of the visual display of FIG. 2, according to one or more additional embodiments.

Referring now to FIG. 12A, with continued reference to FIG. 6, illustrated is another example graphical output of the visual display 206, according to one or more embodiments. More specifically, FIG. 12A depicts another graphical representation of the surgical site 618 as obtained (captured) by the image capture device 310. As illustrated, a portion of tissue 1202 is grasped between the opposing jaws 410, 412 of the end effector 404, and the visual display 206 is augmented with the computer-generated force indicator 704 and associated force vector 708, which provide the real-time magnitude and direction of loading assumed by the end effector 404. In some embodiments, once the end effector 404 clamps down on the tissue 1202, the system may enter tension relief mode, which may activate tissue tension monitoring and the generation of the force indicator 704 to be graphically displayed on the visual display 206.

Optimizing the force vector 708 may entail reducing the magnitude of the force vector 708 and thereby obtaining an optimized force vector 1204. In the illustrated embodiment, this may be accomplished by using a second end effector 1206, depicted in FIG. 12A as a grasper with opposing jaws 1208, 1210. The second end effector 1206 may be maneuvered to the surgical site 618 and the jaws 1208, 1210 may grasp onto the target tissue 1202. The operator (or the computer system 208, or both) may then maneuver the second end effector 1206 until the force vector 708 is minimized to obtain the optimized force vector 1204, which is depicted at or near zero magnitude; i.e., at or near the reference point 706. Accordingly, the loading applied on the second end effector 1206 effectively cancels out or neutralizes the force vector 708, thus leaving the tissue 1202 at the end effector 404 with low tension. In contrast, the tissue 1202 on the opposing side 1212 of the second end effector 1206 may be under high tension.

In some embodiments, grasping onto the target tissue 1202 with the second end effector 1206 may cause the second end effector 1206 to enter tissue relief mode, thus resulting in the generation of a second computer-generated force indicator 1214 and associated force vector 1216, which provide the real-time magnitude and direction of loading assumed by the second end effector 1206. Similar to the force indicator 704 for the first end effector 404, the second force indicator 1214 may be graphically displayed as a three-dimensional (3D) ring (e.g., an orientation ring) that extends about the second end effector 1206 and is tied to the second end effector 1206 at a known reference point 1218. Calculation of the second force vector 1216 may be similar to the calculation of the first force vector 708 and, therefore, will not be described again. Accordingly, the operator (surgeon) may be able to control both end effectors 404, 1206 and watch in real-time on the visual display 206 as the force vector 708 is altered to the optimized force vector 1204.

Figure 12B:
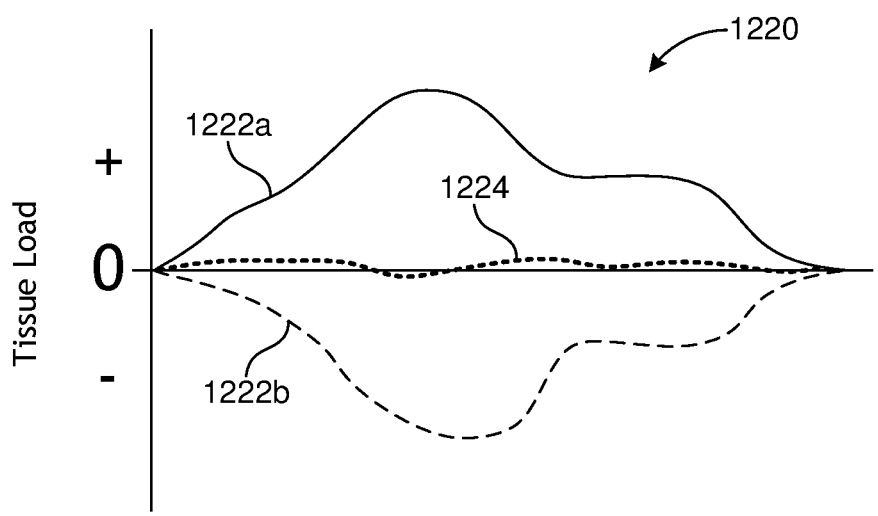
FIG. 12B is a line graph depicting tissue loading on the end effectors of FIG. 12A.

FIG. 12B is a line graph 1220 depicting tissue loading measurement on the end effectors 404, 1206 of FIG. 12A. As illustrated, a first tissue loading 1222a is measured and registered by the first end effector 404, and a second tissue loading 1222b is measured and registered by the second end effector 1206. The first tissue loading 1222a is representative of the first force vector 708 (FIG. 12A) measured at the first end effector 404, and the second tissue loading 1222b is representative of the second force vector 1216 (FIG. 12A) measured at the second end effector 1206. As illustrated, the second tissue loading 1222b effectively neutralizes (counteracts) the first tissue loading 1222a, thereby resulting in a neutralized tissue load 1224 at or near zero. The neutralized tissue load 1224 may be representative of the optimized force vector 1204 (FIG. 12A).

Figure 13:
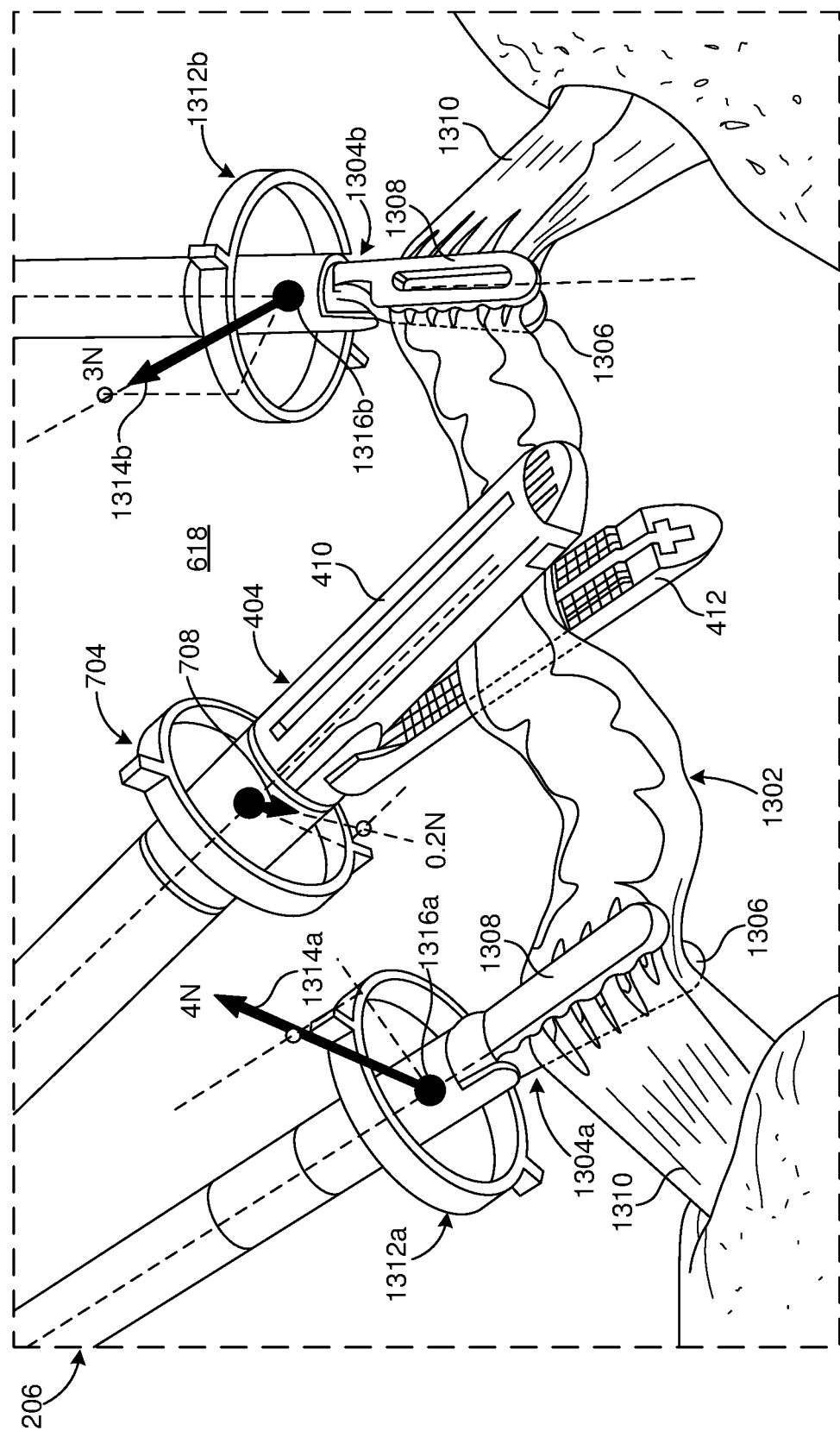
FIG. 13 is another example graphical output of the visual display of FIG. 2, according to one or more additional embodiments.

Referring now to FIG. 13, with continued reference to FIG. 6, illustrated is another example graphical output of the visual display 206, according to one or more embodiments. More specifically, FIG. 13 depicts another graphical representation of the surgical site 618 as obtained (captured) by the image capture device 310. As illustrated, a portion of tissue 1302 is grasped between the opposing jaws 410, 412 of the end effector 404, and the visual display 206 is augmented with the computer-generated force indicator 704 and associated force vector 708, which provide the real-time magnitude and direction of loading assumed on the end effector 404. Once the end effector 404 clamps down on the tissue 1302, the system may enter tension relief mode, which allows the force vector 708 to be initially calculated and graphically displayed to the operator via the visual display 206.

In the illustrated embodiment, optimizing the force vector 708 may entail reducing the magnitude of the force vector 708 so that the end effector 404 can be fired without misaligning staples, etc. As illustrated, this may be accomplished by using two or more additional end effectors, shown as a second end effector 1304a and a third end effector 1304b, each depicted in FIG. 13 as graspers with opposing jaws 1306, 1308. The second and third end effectors 1304a,b may be maneuvered to the surgical site 618 and the jaws 1306, 1308 of each end effector 1304a,b may grasp onto the target tissue 1302 on opposing sides of the first end effector 404. The operator (or the computer system 208, or both) may then maneuver the second and third end effectors 1304a,b to minimize the force vector 708. Accordingly, the combined loading applied by the second and third end effectors 1304a,b effectively neutralizes the force vector 708, thus leaving the tissue 1302 at or near the end effector 404 with low tension. In contrast, the tissue 1302 on the opposing sides 1310 of the second and third end effectors 1304a,b may be under high tension.

In some embodiments, grasping onto the target tissue 1302 with the second and third end effectors 1304a,b may result in the generation of corresponding computer-generated force indicators 1312a and 1312b and associated force vectors 1314a and 1314b, respectively, which provide the real-time magnitude and direction of loading assumed by the second and third end effectors 1304a,b. Similar to the force indicator 704 for the first end effector 404, the second and third force indicators 1312a,b may be graphically displayed as a three-dimensional (3D) ring that extends about the second and third end effectors 1304a,b, respectively, and tied to the second and third end effectors 1304a,b at known reference points 1316a and 1316b, respectively. Calculation of the second and third force vectors 1314a,b may be similar to the calculation of the first force vector 708 and, therefore, will not be described again.

In the illustrated embodiment, the force vector 708 of the end effector 404 is minimized to 0.2 N pointed in a first direction indicated by the first force vector 708. This is accomplished as the second and third end effectors 1304a,b grasp onto and pull the target tissue 1302 in opposing directions. More specifically, the second end effector 1304a pulls on the target tissue 1302 at a magnitude of 4 N in a second direction indicated by the second force vector 1314a, and the third end effector 1304b pulls on the target tissue 1302 at a magnitude of 3 N in a third direction indicated by the third force vector 1314b. The operator (surgeon) may be able to control each end effector 404, 1304a,b and watch in real-time on the visual display 206 as the force vector 708 is minimized. Alternatively, or in addition thereto, the computer system 208 (FIG. 2) may be programmed to operate each of the end effectors 404, 1304a,b to minimize the force vector 708.

Figure 14:
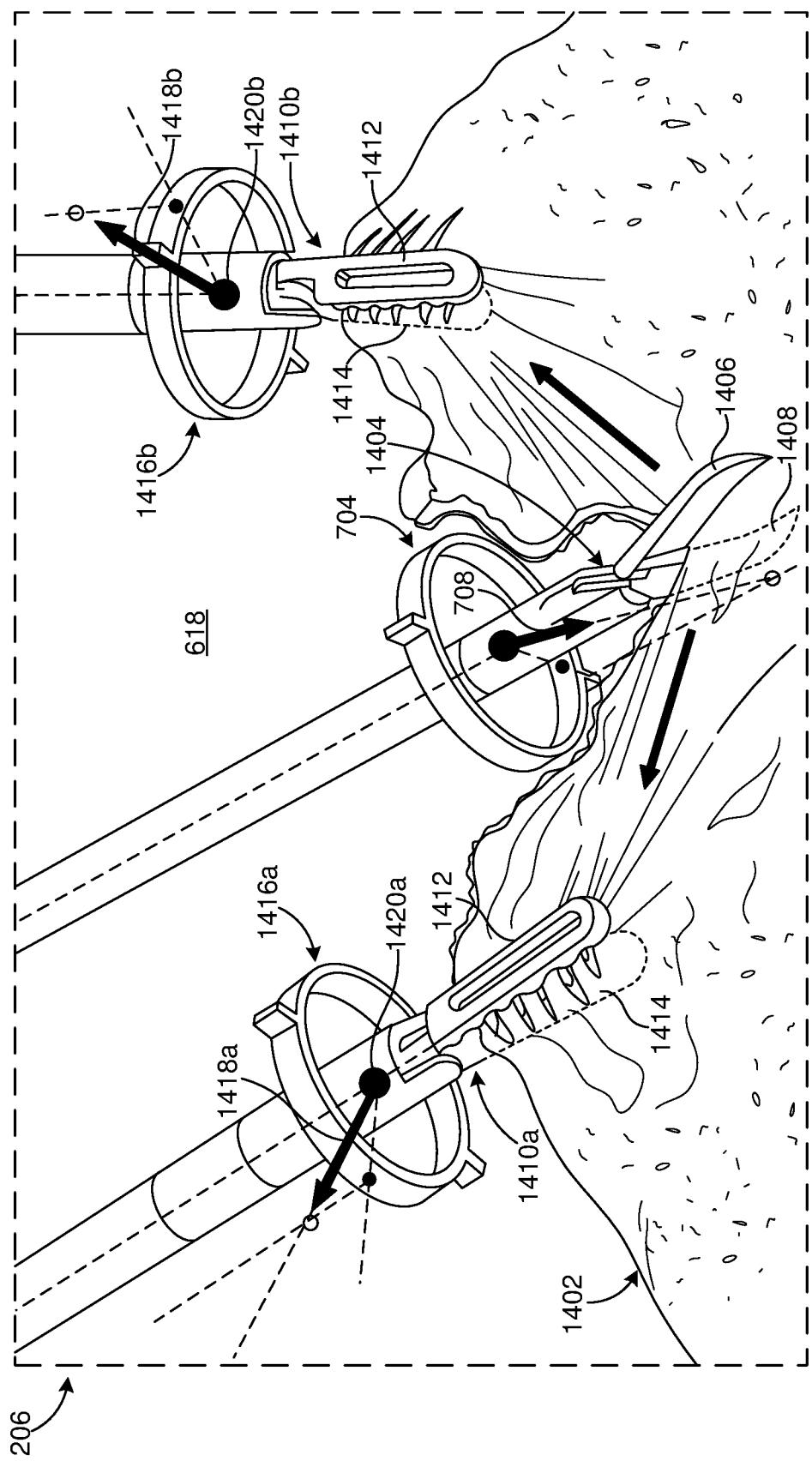
FIG. 14 is another example graphical output of the visual display of FIG. 2, according to one or more additional embodiments.

Referring now to FIG. 14, with continued reference to FIG. 6, illustrated is another example graphical output of the visual display 206, according to one or more embodiments. More specifically, FIG. 14 depicts another graphical representation of the surgical site 618 as obtained (captured) by the image capture device 310. As illustrated, a portion of tissue 1402 (e.g., mesentery tissue) is in the process of being cut by a first end effector 1404, which may comprise surgical scissors having opposing jaws 1406, 1408, alternately referred to as "scissor blades." The visual display 206 is augmented with the computer-generated force indicator 704 and associated force vector 708, which provide the real-time magnitude and direction of loading assumed by the first end effector 1404.

As known in the art, surgical scissors operate more efficiently when cutting through tissue having elevated tension and assuming a normal force down on the tissue. Accordingly, in the present embodiment, it may be desired to increase the tension in the tissue 1402 and simultaneously optimize the force vector 708 such that a normal downward load is supplied by the end effector 1404, which results in an upward load exhibited by the tissue 1402 as the upper scissor blade 1406 pushes downward. As illustrated, this may be accomplished using two or more additional end effectors, shown as a second end effector 1410a and a third end effector 1410b, each depicted in FIG. 14 as graspers with opposing jaws 1412, 1414. The second and third end effectors 1410a,b may be maneuvered to the surgical site 618 and the jaws 1412, 1414 of each end effector 1410a,b may grasp onto the target tissue 1402 on opposing sides of the first end effector 1404. The operator (or the computer system 208, or both) may then maneuver the second and third end effectors 1410a,b in generally opposing directions away from the first end effector 1404, which increases the tension in the target tissue 1402. Furthermore, the first end effector 1404 may be maneuvered such that the force vector 708 points generally downward, which will allow the upper scissor blade 1406 to make a cleaner cut during actuation. As will be appreciated, the force vectors may be switched in alternative embodiments, without departing from the scope of the disclosure. In such embodiments, a normal upward load may be supplied by the end effector 1404, which results in a downward load exhibited by the tissue 1402 as the lower scissor blade 1408 pushes upward.

In some embodiments, grasping onto the target tissue 1402 with the second and third end effectors 1410a,b may result in the generation of corresponding computer-generated force indicators 1416a and 1416b and associated force vectors 1418a and 1418b, respectively, which provide the real-time magnitude and direction of loading assumed by the second and third end effectors 1410a,b. Similar to the force indicator 704 for the first end effector 1404, the second and third force indicators 1416a,b may be graphically displayed as a three-dimensional (3D) ring that extends about the second and third end effectors 1410a,b, respectively, and tied to the second and third end effectors 1410a,b at known reference points 1420a and 1420b, respectively. Calculation of the second and third force vectors 1418a,b may be similar to the calculation of the first force vector 708 and, therefore, will not be described again.

In at least one embodiment, the magnitude of the second and third force vectors 1418a,b may be monitored to ensure that a predetermined maximum tension is not applied on the target tissue 1402. More specifically, approximate tissue properties (e.g., tensile properties) for the target tissue 1402 may be known, and a maximum tensile load may be programmed into the computer system 208 (FIG. 2). During operation, the computer system 208 may continuously monitor the magnitude of the second and third force vectors 1418a,b against the predetermined maximum tensile load, and either send an alert or prevent further movement that would increase the tensile load upon approaching the predetermined maximum tensile load. As will be appreciated, this would prevent excessive force and tearing of the tissue 1402.

Figure 15B:
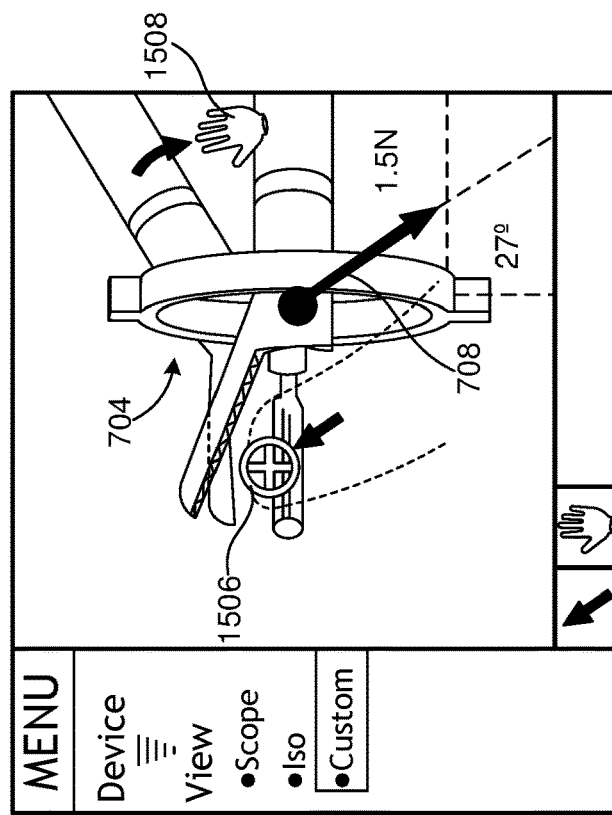
FIG. 15B depicts an example "Custom" view of the visual display of FIG. 15A, according to one or more embodiments.
Figure 15A:
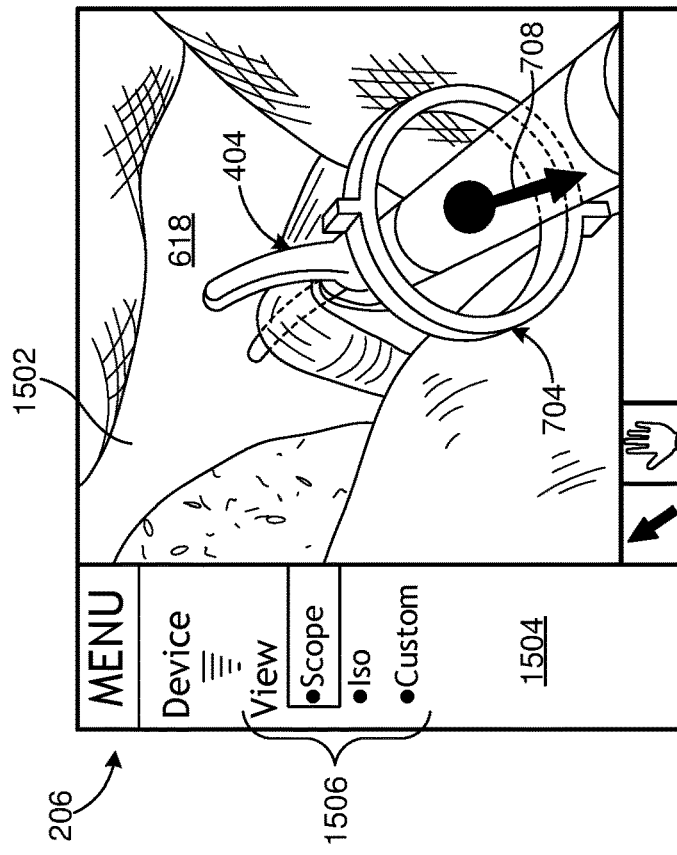
FIG. 15A is one example of the visual display of FIG. 2, according to one or more embodiments.

FIG. 15A is one example of the visual display 206 of FIG. 2, according to one or more embodiments. As illustrated, the visual display 206 may include or otherwise provide a viewing screen 1502. Images captured by the image capture device 310 (FIG. 6) may be displayed on the viewing screen 1502, thus enabling the operator (surgeon) to view the surgical site 618 in real-time. The computer-generated force indicator 704 and the associated force vector 708 may also be augmented onto the visual display 206 at the viewing screen 1502, thus providing the operator with a graphical representation of the magnitude and direction of loading assumed by the end effector 404 in real-time.

The visual display 206 may further include a graphical user interface (GUI) 1504 that includes a menu of user-selectable options 1506. In the illustrated embodiment, the options 1506 provided on the GUI 1504 allow the user to alter the view displayed on the viewing screen 1502. In FIG. 15A, the "Scope" view is selected, and the viewing screen 1502 correspondingly displays images captured by the image capture device 310 (FIG. 6). In some cases, however, the image capture device 310 (FIG. 6) may be positioned such that the force indicator 704 might provide ambiguous load direction for the force vector 708, thus making it difficult for the operator to determine how to maneuver the end effector 404 to optimize the force vector 708. Since the image capture device 310 is located in a single location relative to the surgical site 618, no other real-time views of the surgical site 618 are available unless the image capture device 310 changes position or another image capture device 310 is introduced to provide an alternative perspective of the surgical site 618 alter the perspective. In such cases, the operator may select "Iso" view or "Custom" view.

According to the present disclosure, the "Iso" and "Custom" views may be selected to graphically change the perspective displayed on the viewing screen 1502 to an isometric or custom view, respectively, of the surgical site 618. The "Iso" and "Custom" views may not be actual views of the surgical site 618, but may instead comprise three-dimensional (3D) models graphically generated by the computer system 208 (FIG. 2). More particularly, the computer system 208 may be programmed to graphically replicate the "Scope" view of the surgical site 618 in 3D, and enable dynamic control of the resulting graphical representation to facilitate viewing of the surgical site 618 from various vantage points offset from the "Scope" view. Accordingly, the "Iso" view may be a predetermined isometric view of the graphically replicated "Scope" view of the surgical site 618. In contrast, the "Custom" view may provide the operator with the ability to manually alter the graphically replicated "Scope" view to a desired "custom" vantage point. The "Iso" and "Custom" views may be similar in some respects to manipulating the views of 3D CAD models using conventional CAD modeling software.

FIG. 15B depicts an example "Custom" view of the visual display 206, according to one or more embodiments. In some embodiments, when the "Custom" view option is selected, the operator may be able to identify a pivot point 1506 on the graphically replicated "Scope" view provided on the viewing screen 1502 and rotate the view about the pivot point 1506 to a desired angular configuration. In some embodiments, the operator may be able to select and use a "hand" icon 1508 to "grab" onto and adjust the view. In FIG. 15B, the graphically replicated "Scope" view has been rotated such that a side view of the end effector 404 is displayed, which provides a clearer depiction of the force indicator 704 and the load direction of the force vector 708. As will be appreciated, the "Custom" view (or the "Iso" view) may allow the operator to more easily judge where the current force vector 708 lies and how best to optimize the force vector 708.

FIGS. 16A-16C depict example operation of scaling down movement of an end effector 1602, according to one or more embodiments. More specifically, FIG. 16A depicts a user input device 1604 that can be grasped and manipulated in space by a hand 1606 of an operator (surgeon), and FIGS. 16B and 16C depict corresponding scaled-down movement of the end effector 1602 in response to movement (manipulation) of the user input device 1604. The end effector 1602 may comprise any type of end effector mentioned herein and may be maneuvered to engage a bodily structure 1608 (e.g., tissue, an organ, etc.) based on movement of the user input device 1604. The user input device 1604 may comprise a type of joystick or controller that can be grasped by the hand 1606 between two or more fingers and/or the palm of the hand 1606. However, the user input device 1604 may comprise any type of user input device mentioned herein, without departing from the scope of the disclosure.

The user input device 1604 may be in communication with the computer system 208 (FIG. 2), which may be programmed and otherwise configured to receive input signals from the user input device 1604 caused by the operator manipulating the user input device 1604 with the hand 1606. The computer system 208 may then convert the input signals into corresponding movement of the end effector 1602. In some embodiments, movement of the end effector 1602 may be directly proportional in degree and magnitude to the corresponding movement of the user input device 1604. In such embodiments, movement of the user input device 1604 may be replicated on a 1-to-1 ratio with identical movement of the end effector 1602.

In other embodiments, however, the computer system 208 may be programmed to "scale down" movement of the end effector 1602 based on input signals from the user input device 1604. As a result, the actual movement of the end effector 1602 may be a fraction of the actual movement of the user input device 1604. More specifically, the magnitude of the movement of the user input device 1604 may be "x," as depicted in FIG. 16A. In contrast, as shown in FIG. 16B, the corresponding movement of the end effector 1604 may be "$x/y_1$," which constitutes a fraction of movement x. In other embodiments, as shown in FIG. 16C, the corresponding movement of the end effector 1604 may be "$x/y_2$," which may comprise a smaller fraction of movement x.

In at least one embodiment, the computer system 208 (FIG. 2) may be directed to scale down movement (alternately referred to as "control scaled' movement) of the end effector 1602 when the system enters the tension relief mode. In this mode, the operator will be required to move the hand 1606 to a larger degree to obtain an equivalent amount of movement or distance at the end effector 1602. As will be appreciated, this may prove advantageous in honing in on the bodily structure 1608 with increased accuracy, and reducing the chance of inadvertent movement of the end effector 1602 or overcorrecting of the target force vector 708 that might unintentionally damage the bodily structure 1608. This embodiment is similar to proportional only or proportional/integral control theory commonly used in systems engineering and process control applications.

FIG. 17 is a schematic flowchart of another example method 1700 of optimizing loading on a surgical tool end effector, according to one or more embodiments. The method 1700 may be used, for example, in operating the system shown in FIGS. 6 and 7 and, more particularly, in optimizing the tissue tension and force vector 708 (FIG. 7) assumed by the end effector 404 (FIGS. 4 and 6) of the surgical tool 400 (FIGS. 4 and 6). Accordingly, the following discussion of the method 1700 will reference the parts and features depicted in FIGS. 6 and 7. It will be appreciated, however, that the method 1700 may be used with other systems and surgical tools, such as those shown in FIGS. 12A, 13, and 14, without departing from the scope of the disclosure.

The method 1700 may allow an operator (surgeon) to manually optimize the force vector 708 by manually manipulating one or more user input devices. Accordingly, in some embodiments, the method 1700 may optionally start with the operator selecting "manual mode," as at 1702. As discussed above, "manual mode" may be selected by the operator via a selector (e.g., the selector 1000 of FIG. 10). Once in manual mode, the operator may manipulate the user input devices to alter the orientation of the end effector 404 in real-time and thereby achieve desired orientations. The operator may view the surgical site 618 and the end effector 404 as it moves via the visual display 206 (FIG. 2), which provides images captured by the image capture device 310 (FIG. 6).

The method 1700 may further include calculating a tissue tension assumed on the end effector 404 and displaying a corresponding force vector 708 representative of the tissue tension, as at 1704. In some embodiments, the tissue tension may be calculated once the system enters the tension relief mode, which may be activated by clamping down on the target tissue 702 with the end effector 404. The force vector 708 may be calculated as generally described above and, therefore, will not be described again in detail. The force vector 708 may be graphically augmented onto the visual display 206 as part of the force indicator 704, as also generally described above.

The operator may then maneuver the end effector 404 via the user input devices to adjust the tissue tension and optimize the force vector 708, as at 1706. In some embodiments, this may entail minimizing the tissue tension by minimizing the force vector 708, which may be accomplished by altering the configuration and/or position of the end effector 404, or in conjunction with one or more additional end effectors, as generally described above. In other embodiments, however, optimizing the tissue tension may entail increasing the tissue tension and/or directing the force vector 708 in a desired direction with a desired magnitude, which might also require the use of one or more additional end effectors, as described above.

Once a desired or predetermined tissue tension and/or force vector 708 is achieved, as at 1708, the operator may proceed with the procedure and fire the end effector 404, as at 1710. If the desired or predetermined tissue tension and/or force vector 708 is not achieved, however, as at 1708, the method 1700 returns to step 1706 where the operator maneuvers the end effector 404 again in an attempt to optimize the tissue tension and/or force vector 708.

FIG. 18 is a schematic flowchart of another example method 1800 of optimizing loading on a surgical tool end effector, according to one or more embodiments. Similar to the method 1700 of FIG. 17, the method 1800 may be used in operating the system shown in FIGS. 6 and 7 and, more particularly, in optimizing the force vector 708 (FIG. 7) assumed by the end effector 404 (FIGS. 6 and 7) of the surgical tool 400 (FIGS. 4 and 6). Accordingly, the following discussion of the method 1800 will reference the parts and features depicted in FIGS. 6 and 7. It will be appreciated, however, that the method 1800 may be used with other systems and surgical tools, such as those shown in FIGS. 12A, 13, and 14, without departing from the scope of the disclosure.

The method 1800 may facilitate semi-automatic optimization of the force vector 708. Accordingly, in some embodiments, the method 1800 may optionally start with the operator selecting "semi-automatic mode," as at 1802. As discussed above, "semi-automatic mode" may be selected by the operator via a selector (e.g., the selector 1000 of FIG. 10). Once in semi-automatic mode, the operator may manipulate user input devices to alter the orientation of the end effector 404 in real-time and thereby achieve desired orientations. The operator may view the surgical site 618 and the end effector 404 as it moves via the visual display 206 (FIG. 2), which provides images captured by the image capture device 310 (FIG. 6).

After the end effector 404 grasps or otherwise engages target tissue, the method 1800 may include calculating a tissue tension assumed on the end effector 404 and displaying a corresponding force vector 708 representative of the tissue tension, as at 1804. In some embodiments, grasping or engaging the target tissue may cause the system to enter the tension relief mode, which enables the tissue tension to be calculated. The force vector 708 may be calculated as generally described above and, therefore, will not be described again. The force vector 708 may be graphically augmented onto the visual display 206 as part of the force indicator 704, as also generally described above.

Once the force vector 708 is calculated, the method 1800 may optionally include scaling down movement of the end effector 404, as at 1806. As discussed above, scaling down end effector 404 movement may prove advantageous in providing the operator with increased accuracy in optimizing the force vector 708, and reducing the chance of inadvertent movement of the end effector 404 that might otherwise cause damage the target tissue.

The operator and the system may then cooperatively maneuver the end effector 404 via the user input devices to adjust the tissue tension and optimize the force vector 708, as at 1808. In some embodiments, this may entail minimizing the tissue tension by minimizing the force vector 708, which may be accomplished by altering the configuration and/or position of the end effector 404, or in conjunction with one or more additional end effectors, as generally described above. In other embodiments, however, optimizing the tissue tension may entail increasing the tissue tension and/or directing the force vector 708 in a desired direction with a desired magnitude, which might also require the use of one or more additional end effectors, as described above. In at least one embodiment, the operator maneuvers the user input devices and programs a desired force vector, and the computer system 208 (FIG. 2) subsequently directs movement of the end effector 404 to optimize the force vector 708 to the desired force vector.

Once the desired or predetermined tissue tension and/or force vector 708 is achieved, as at 1810, the operator may proceed with the procedure and fire the end effector 404, as at 1812. If the desired or predetermined tissue tension and/or force vector 708 is not achieved, however, as at 1810, the method 1800 returns to step 1808 where the operator maneuvers the end effector 404 again in an attempt to optimize the tissue tension and/or force vector 708.

FIG. 19 is a schematic flowchart of another example method 1900 of optimizing loading on a surgical tool end effector, according to one or more additional embodiments. Similar to the methods 1700 and 1800 of FIGS. 17 and 18, the method 1900 may be used in operating the system shown in FIGS. 6 and 7 and, more particularly, in optimizing the force vector 708 (FIG. 7) assumed by the end effector 404 (FIGS. 6 and 7) of the surgical tool 400 (FIGS. 4 and 6). Accordingly, the following discussion of the method 1900 will reference the parts and features depicted in FIGS. 6 and 7. It will be appreciated, however, that the method 1900 may be used with other systems and surgical tools, such as those shown in FIGS. 12A, 13, and 14, without departing from the scope of the disclosure. For example, the method 1900 may be particularly applicable to operation of the end effector 1404 (i.e., surgical scissors) of FIG. 14.

The method 1900 may facilitate automatic optimization of the force vector 708 under the control of the computer system 208 (FIG. 2). Accordingly, in some embodiments, the method 1900 may optionally start with the operator selecting "automatic mode," as at 1902. As discussed above, "automatic mode" may be selected by the operator via a selector (e.g., the selector 1000 of FIG. 10). In automatic mode, a desired force vector to be assumed on the end effector 404 may be set, as at 1904. In some embodiments, the operator may input the desired magnitude and direction for the force vector 708 into the computer system 208 (FIG. 2), such as via a graphical user interface or the like.

In other embodiments, however, upon attaching the surgical tool 400 (FIG. 6) to the tool driver 608 (FIG. 4) for use, the computer system 208 may automatically recognize and know the type of tool being used based on system recognition protocols. In such embodiments, the computer system 208 may be programmed with certain preferred parameters of operation and predetermined force vectors 708 matching the particular end effector 404 associated with the surgical tool 400. For surgical scissors, for example, the computer system 208 may be programmed to achieve a desired force vector 708 that provides a normal load down. In contrast, for surgical staplers, the computer system 208 may be programmed to achieve a desired force vector 708 having minimal magnitude and torque, and preferably providing axial tension along the longitudinal axis $A_2$ (FIGS. 4 and 7) of the end effector 404.

The end effector 404 may then be maneuvered to the surgical site 618 and the operator may view the surgical site 618 and the end effector 404 as it moves via the visual display 206 (FIG. 2). Alternatively, the end effector 404 may already be at the surgical site 618 and the desired force vector may be set while at the surgical site 618. The operator or the computer system 208 (or both) may direct the end effector 404 to the surgical site 618.

After the end effector 404 grasps or otherwise engages target tissue, the method 1900 may include calculating a tissue tension assumed on the end effector 404 and displaying a corresponding force vector 708 representative of the tissue tension, as at 1906. Grasping or engaging the target tissue may cause the system to enter the tension relief mode, which enables the tissue tension and the corresponding force vector 708 to be calculated. As described herein, the calculated force vector 708 may be graphically augmented onto the visual display 206 as part of the force indicator 704.

Once the force vector 708 is calculated, the method 1900 may optionally include scaling down movement of the end effector 404, as at 1908. The computer system 208 (FIG. 2) may then maneuver the end effector 404 to adjust the tissue tension and optimize the force vector 708, as at 1910. More specifically, the computer system 208 may direct the robotic arm 606 and the surgical tool 400 to move the end effector 404 and achieve the desired force vector 708 programmed by the operator. In some embodiments, this may entail minimizing the tissue tension by minimizing the force vector 708, which may be accomplished by altering the configuration and/or position of the end effector 404, or in conjunction with one or more additional end effectors, as generally described above. In other embodiments, however, optimizing the tissue tension may entail increasing the tissue tension and/or directing the force vector 708 in a desired direction with a desired magnitude, which might also require the use of one or more additional end effectors, as described above.

Once the desired or predetermined tissue tension and/or force vector 708 is achieved, as at 1912, the operator may proceed with the procedure and fire (actuate) the end effector 404, as at 1914. If the desired or predetermined tissue tension and/or force vector 708 is not achieved, however, as at 1912, the method 1900 returns to step 1912 where the computer system 208 (FIG. 2) directs movement of the end effector 404 to adjust the tissue tension and optimize the force vector 708.

In some embodiments, the desired force vector 708 on the end effector 404 (FIGS. 6 and 7) may be maintained during firing, as at 1916. More specifically, the computer system (FIG. 2) may be constantly measuring and refining the force vector 708 (i.e., tissue tension) through the clamping and firing stages. In some embodiments, the computer system 208 may be programmed to stop in the middle of a cutting or firing process to adjust the tension and ensure the desired (optimized) force vector is achieved. As will be appreciated, automatic reduction and/or balancing of the force vector 708 during firing may prove advantageous in counteracting the effect of tip movement of the end effector 404, which may occur due to internal firing forces.

FIG. 20 is a schematic flowchart of another example method 2000 of optimizing loading on a surgical tool end effector, according to one or more additional embodiments. Similar to the methods 1700-1900 of FIGS. 17-19, respectively, the method 2000 may be used in operating the system shown in FIG. 6, but may also be used in operating the system shown in FIG. 14. More particularly, the method 2000 may be used to set the force vector 708 (FIG. 14) to be assumed by the end effector 1404 (FIG. 14) during operation. Accordingly, the following discussion of the method 2000 will reference the parts and features depicted in FIGS. 6 and 14.

The method 2000 may encompass setting and automatic optimization of the force vector 708 under the control of the computer system 208 (FIG. 2). Accordingly, in some embodiments, the method 2000 may optionally start with the operator selecting "automatic mode," as at 2002. In automatic mode, a desired force vector to be assumed on the end effector 1404 during operation may be set, as at 2004. In some embodiments, the operator may input the desired magnitude and direction for the desired force vector into the computer system 208 (FIG. 2), such as via a graphical user interface or the like.

In other embodiments, however, upon attaching the surgical tool 400 (FIG. 6) to the tool driver 608 (FIG. 4) for use, the computer system 208 may automatically recognize and know the type of tool being used based on system recognition protocols. In such embodiments, the computer system 208 may be programmed with certain preferred parameters of operation and predetermined force vectors matching the particular end effector 1404 associated with the surgical tool 400. For surgical scissors, for example, the computer system 208 may be programmed to achieve a desired force vector that provides a normal load down. In contrast, for surgical staplers, the computer system 208 may be programmed to achieve a desired force vector having minimal magnitude and torque, and preferably providing axial tension along the longitudinal axis $A_2$ (FIGS. 4 and 7) of the end effector 1404.

In some embodiments, the method 2000 may optionally include setting limits on the magnitude and/or the direction for the desired force vector, as at 2006. As will be appreciated, limiting the magnitude of the desired force vector may prove advantageous in preventing the end effector 1404 from inadvertently tearing the tissue with excessive loading. Limiting the direction of the desired force vector may prove advantageous in directing the end effector 1404 in a known direction, and preventing inadvertent contact with adjacent critical structures.

The end effector 1404 may then be maneuvered to the surgical site 618 and the operator may view the surgical site 618 and the end effector 1404 as it moves via the visual display 206 (FIG. 2). Alternatively, the end effector 1404 may already be at the surgical site 618 and the desired force vector may be set (input) while at the surgical site 618. The operator or the computer system 208 (or both) may direct the end effector 1404 to the surgical site 618.

After the end effector 1404 engages target tissue at the surgical site 618, the method 2000 may include calculating a tissue tension assumed on the end effector 1404 and displaying a corresponding force vector 708 representative of the tissue tension, as at 2008. Engaging the target tissue may cause the system to enter the tension relief mode, which enables the tissue tension and the corresponding force vector 708 to be calculated and graphically augmented onto the visual display 206 as part of the force indicator 704.

Once the force vector 708 is calculated, the end effector 1404 may be maneuvered to optimize the force vector 708 to obtain the programmed desired force vector, as at 2010. More specifically, the computer system 208 (FIG. 2) may direct one or both of the robotic arm 606 and the surgical tool 400 to move the end effector 1404 and achieve the desired force vector 708 programmed by the operator. In some embodiments, obtaining the desired force vector may entail increasing the tension in the tissue and/or directing the force vector 708 in the desired direction with the desired magnitude, which might require the use of one or more additional end effectors, as described herein. In at least one embodiment, achieving the desired force vector may occur while the end effector 1404 is be fired (actuated).

Once the desired force vector is achieved, as at 2012, the operator may proceed with the procedure and fire (actuate) the end effector 1404, as at 2014. With surgical scissors, firing (actuating) the end effector 1404 may entail advancing the end effector 1404 through the tissue while repeatedly opening and closing the opposing jaws 1406, 1408 (FIG. 14) to transect (cut) the tissue. If the desired force vector is not achieved, however, as at 2012, the method 2000 returns to step 2010 where the computer system 208 (FIG. 2) directs movement of the end effector 1404 to adjust the tissue tension and optimize the force vector 708.

In some embodiments, the desired force vector 708 on the end effector 1404 may be maintained during firing, as at 2016. More specifically, the computer system (FIG. 2) may be constantly measuring and refining the force vector 708 (i.e., tissue tension) through the firing stage. In some embodiments, the computer system 208 may be programmed to stop in the middle of the cutting or firing process to adjust the tension and ensure the desired (optimized) force vector is achieved. As will be appreciated, automatic reduction and/or balancing of the force vector 708 during firing may prove advantageous in counteracting the effect of tip movement of the end effector 1404, which may occur due to internal firing forces.

Figure 21:
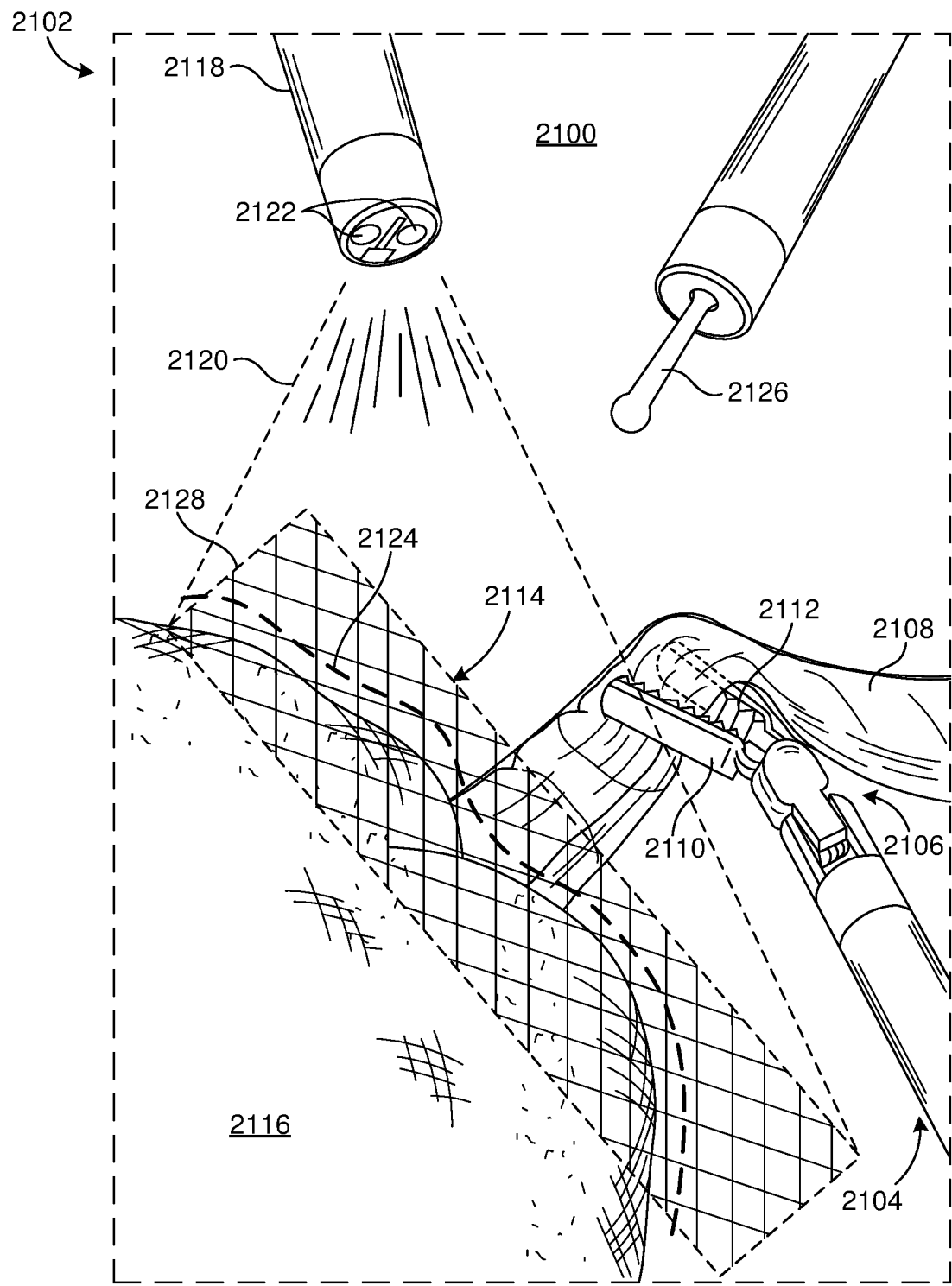
FIG. 21 is an enlarged view of an example surgical site displayed on an example visual display, according to one or more embodiments.

FIG. 21 is an enlarged view of an example surgical site 2100 displayed on an example visual display 2102, according to one or more embodiments. The surgical site 2100 may be the same as or similar to the surgical site 618 of FIG. 6, and the visual display 2102 may be the same as or similar to the visual display 206 of FIG. 2. Accordingly, the visual display 2102 may provide a graphical output of the images captured by the image capture device 310 (FIG. 6). A surgical tool 2104 including an end effector 2106 is portrayed in the visual display 2102, and a portion of tissue 2108 is grasped between opposing jaws 2110, 2112 of the end effector 2106. While depicted in FIG. 21 as a grasper tool, the end effector 2106 may alternatively comprise any of the end effectors mentioned herein, without departing from the scope of the disclosure.

According to embodiments of the present disclosure, one or more sensitive or "restricted" zones 2114 may be defined, generated, or otherwise provided at the surgical site 2100. The restricted zones 2114 (alternately referred to as "no-go" or "no-fly" zones) may comprise areas at or near the surgical site 2100 designed to help protect a critical structure 2116 from mechanical, electrical or thermal trauma (damage) caused by the end effector 2106 or any other surgical tool that might be used at the surgical site 2100. Example critical structures 2116 include, but are not limited to, the liver, the lungs, arteries, ureters, nerves, or any combination thereof.

As illustrated, the restricted zone 2114 may be defined on, over, or about the critical structure 2116, and may generally interpose the critical structure 2116 and the end effector 2106. Once the restricted zone 2114 is defined (created), the end effector 2106 may be prevented (prohibited) from entering, violating, and/or encroaching upon the restricted zone 2114, thereby protecting the critical structure 2116 from potential contact with the end effector 2106. In some embodiments, the computer system 208 (FIG. 2) may be configured to generate warnings or alerts (e.g., audible, visual, tactile, etc.) when the end effector 2106 approaches the restricted zone 2114. Such warnings may become more intense as the end effector 2106 closes in on the restricted zone 2114. In at least one embodiment, the computer system 208 may be programmed to disable operation if the restricted zone 2114 is reached or penetrated (breached).

In some embodiments, the restricted zone 2114 may be defined by or otherwise created using structured light. In such embodiments, a structured light source 2118 may be advanced to the surgical site 2100 and configured to emit structured light 2120 in a known pattern or grid onto the critical structure 2116. The structured light 2120 deforms when striking the varying outer surfaces of the critical structure 2116, and a camera 2122 is able to perceive and calculate the contours (e.g., the depth and the surface information) of the critical structure 2116 based on the severity of the deformed pattern of the structured light 2120 impinging upon the critical structure 2116. In some embodiments, the structured light 2120 may comprise visible light and the camera 2122 may be designed to perceive the visible light. In other embodiments, however, the structured light 2120 may comprise non-visible light (e.g., infrared, ultraviolet, X-ray, gamma ray, etc.) and the camera 2122 may be designed to perceive or detect such non-visible light. Using non-visible light may be advantageous in that it may not interfere with operation of the image capture device 310 (FIG. 6), for which the projected pattern may be confusing.

The structured light source 2118 and the camera 2122 may each communicate with the computer system 208 (FIG. 2), which may be programmed to direct and operate the structured light source 2118 and the camera 2122. Data captured by the camera 2122 may be received at the computer system 208, which may be programmed to calculate the contours (e.g., the depth and surface information) of the critical structure 2116 and thereby generate a contoured barrier 2124. The contoured barrier 2124 may comprise a three-dimensional (3D) plane that generally follows the outer form of the critical structure 2116 and thereby defines the restricted zone 2114. The computer system 208 may be programmed to prevent (prohibit) the end effector 2106 from penetrating the contoured barrier 2124 and thereby entering, violating, and/or encroaching upon the restricted zone 2114.

In some embodiments, the contoured barrier 2124 may be graphically displayed on the visual display 2102 to provide the user with a computer-generated representation of the restricted zone 2114. In such embodiments, the operator may operate the end effector 2106 such that it does not visibly penetrate the contoured barrier 2124. In other embodiments, however, the contoured barrier 2124 may not be visibly displayed on the visual display 2102, and the computer system 202 may instead be programmed to prevent (prohibit) the end effector 2106 from penetrating the contoured barrier 2124.

The contoured barrier 2124 that defines the restricted zone 2114 may alternatively be defined by or otherwise created using a touch probe 2126. In such embodiments, the touch probe 2126 may be advanced to the surgical site 2100 and caused to contact or engage a plurality of surfaces of the critical structure 2116. A data point is created each instance the touch probe 2126 contacts the critical structure 2116, and each data point corresponds to the depth and contour of the critical structure 2116 at the specific coordinates of the engagement location. The touch probe 2126 may communicate with the computer system 208 (FIG. 2), and after a plurality of data points are captured (recorded) with the touch probe 2126, the computer system 208 may generate the contoured barrier 2124 that defines the restricted zone 2114.

In other embodiments, the restricted zone 2114 may be defined by or otherwise created as a planar barrier 2128, alternately referred to as a "straight line" barrier. In such embodiments, the touch probe 2126 may be used to capture or record a minimum of three contact points in space adjacent the critical structure 2116. The computer system 208 (FIG. 2) may then be programmed to connect the three contact points and generate the planar barrier 2128 in the form of a two-dimensional (2D) plane. The computer system 208 may be programmed to prevent (prohibit) the end effector 2106 from penetrating the planar barrier 2128 and thereby entering, violating, and/or encroaching upon the restricted zone 2114.

In some embodiments, the planar barrier 2128 generated with the touch probe 2126 may be graphically displayed on the visual display 2102 to provide the user with a computer-generated representation of the restricted zone 2114. In such embodiments, the operator may operate the end effector 2106 such that it does not visibly penetrate the planar barrier 2128. In other embodiments, however, the planar barrier 2128 may not be displayed on the visual display 2102, and the computer system 202 may be programmed to prevent (prohibit) the end effector 2106 from penetrating the planar barrier 2128.

The planar barrier 2128 that defines the restricted zone 2114 may alternatively be defined by or otherwise created manually by the operator (surgeon). In one embodiment, for example, the operator may decouple from the user input devices that operate the end effector 2106 and engage a mouse tool or other GUI-operated device that allows the operator to create the planar barrier 2128 in the form of a 2D plane in the image displayed on the visual display 2102. The computer system 208 (FIG. 2) may be capable of supporting such graphical augmentation to the visual display 2102. The size and orientation of the graphically-created planar barrier 2128 may then be altered as needed by the operator, and subsequently placed in a location to generally interpose the critical structure 2116 and the end effector 2106.

In another embodiment, the visual display 2102 may also operate as a telestrator, and the computer system 208 (FIG. 2) may be programmed to facilitate and support telestration via the visual display 2102. In such embodiments, the operator (surgeon) may be able to draw (e.g., a free hand sketch or the like) a 2D structure (e.g., a plane or a line) directly on the screen of the visual display 2102, such as through the use of a touchscreen technology or an electronic pen that interacts with the visual display 2102. The drawing signal may be communicated to the computer system 208, which overlays the drawing on the video image already present on the visual display 2102 and outputs the combined signal for display. The resulting drawn image may comprise the planar barrier 2128 (or the contoured barrier 2124).

In yet other embodiments, the restricted zone 2114 may be defined or otherwise created using a variety of scanning techniques such as, but not limited to, ultrasound, a computerized tomography (CT) scan, an X-ray, a magnetic resonance imaging (MRI) scan, or endoscopic data obtained from a patient exam prior to the surgery. In such embodiments, coordinates for a 3-dimensional restricted zone or cube may be obtained and otherwise established from the aforementioned scanning techniques. The location and size of a tumor, for example, may be obtained from one of the scanning techniques and, subsequently, the operator may establish the restricted zone by selecting a distance away from the identified tumor in x, y and z directions. The computer system 208 may then be programmed to prevent (prohibit) the end effector 2106 from entering, violating, and/or encroaching upon the restricted zone 2114. Otherwise, the computer system 208 may be programmed to allow the end effector 2106 to enter the restricted zone 2114 to excise the tumor.

In some embodiments, the restricted zone 2114 may not only protect the critical structure 2116 against physical trespasses or penetrations, e.g., via the end effector 2106 physically breaching the restricted zone 2114, but may also protect against non-physical trespasses or violations caused by non-physical elements. In one or more embodiments, for example, the restricted zone 2114 may be breached via a thermal trespass or violation. More particularly, some types of end effectors, such as ultrasonic, bipolar and/or monopolar instruments (e.g., utilizing RF energy, generate elevated temperatures during operation. In some cases, such elevated temperatures (e.g., a non-physical element) may propagate (radiate) toward and potentially damage the critical structure 2116, which may be particularly sensitive to thermal gradients. In such embodiments, the restricted zone 2114 may be defined by and otherwise monitored with a thermal detector in communication with the computer system 208. In at least one embodiment, the thermal detector may comprise an infrared camera or the like built into the image capture device 310 (FIG. 6) or a separate device advanced to the surgical site 2100 to monitor heat transfer. When the thermal detector detects that the restricted zone 2114 has been thermally breached, the computer system 208 may send an alert (e.g., audible, visual, tactile, etc.) to the operator (surgeon), or may disable operation to prevent damage to the critical structure 2116.

In other embodiments, the restricted zone 2114 may be breached via electrical arcing (e.g., a non-physical element). More particularly, some types of end effectors, such as monopolar electrodes, can generate electrical arc flashing during operation. In some cases, the electrical discharge may propagate toward and contact the critical structure 2116. In such embodiments, the restricted zone 2114 may be defined by and otherwise monitored with a temperature sensor, an optical sensor, a flash sensor, or the like in communication with the computer system 208. When it is detected that the restricted zone 2114 has been breached via electrical arcing, the computer system 208 may send an alert (e.g., audible, visual, tactile, etc.) to the operator (surgeon), or may disable operation to prevent further damage to the critical structure 2116. In yet other embodiments, the electrosurgical generator used to provide electrical energy to the surgical site may be used as a monitor/sensor by detecting rapid changes in current/voltage associated with arcing. The generator can also be in communication with the computer system 208 which could automatically lower or cease the electrical output if an arc is detected.

Figure 22:
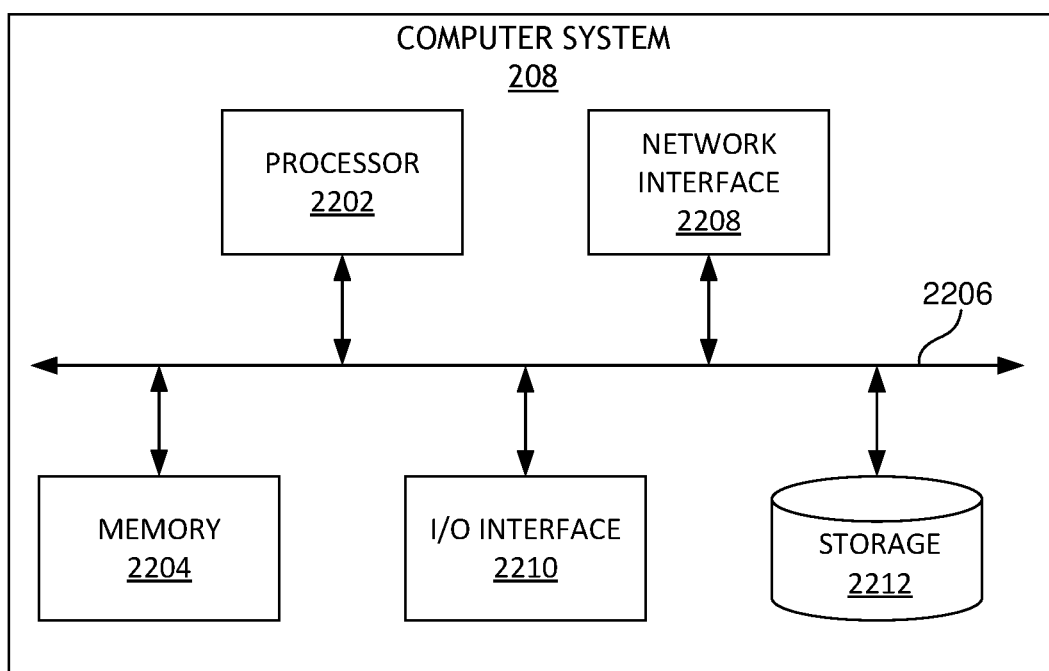
FIG. 22 is an example schematic diagram of the computer system of FIG. 2.

FIG. 22 is an example schematic diagram of the computer system 208 of FIG. 2. The systems, devices, and methods disclosed herein can be implemented using the computer system 208, which may also be referred to herein as a digital data processing system or programmable system. One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and programmable logic devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The computer system 208 shown in FIG. 22 includes one or more processors 2202, which can control the operation of the computer system 208. "Processors" are also referred to herein as "controllers." The processor(s) 2202 can include any type of microprocessor or central processing unit (CPU), including programmable general-purpose or special-purpose microprocessors and/or any one of a variety of proprietary or commercially available single or multi-processor systems. The computer system 208 can also include one or more memories 2204, which can provide temporary storage for code to be executed by the processor(s) 2202 or for data acquired from one or more users, storage devices, and/or databases. The memory 2204 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 208 can be coupled to a bus system 2206. The illustrated bus system 2206 is an abstraction that represents any one or more separate physical busses, communication lines/interfaces, and/or multi-drop or point-to-point connections, connected by appropriate bridges, adapters, and/or controllers. The computer system 208 can also include one or more network interface(s) 2208, one or more input/output (IO) interface(s) 2210, and one or more storage device(s) 2212.

The network interface(s) 2208 can enable the computer system 208 to communicate with remote devices, e.g., other computer systems, over a network, and can be, for non-limiting example, remote desktop connection interfaces, Ethernet adapters, and/or other local area network (LAN) adapters. The IO interface(s) 2210 can include one or more interface components to connect the computer system 208 with other electronic equipment. For non-limiting example, the IO interface(s) 2210 can include high-speed data ports, such as universal serial bus (USB) ports, 1394 ports, Wi-Fi, Bluetooth, etc. Additionally, the computer system 208 can be accessible to a human user, and thus the IO interface(s) 2210 can include displays, speakers, keyboards, pointing devices, and/or various other video, audio, or alphanumeric interfaces. The storage device(s) 2212 can include any conventional medium for storing data in a non-volatile and/or non-transient manner. The storage device(s) 2212 can thus hold data and/or instructions in a persistent state, i.e., the value(s) are retained despite interruption of power to the computer system 208. The storage device(s) 2212 can include one or more hard disk drives, flash drives, USB drives, optical drives, various media cards, diskettes, compact discs, and/or any combination thereof and can be directly connected to the computer system 208 or remotely connected thereto, such as over a network. In an exemplary embodiment, the storage device(s) 2212 can include a tangible or non-transitory computer readable medium configured to store data, e.g., a hard disk drive, a flash drive, a USB drive, an optical drive, a media card, a diskette, a compact disc, etc.

The elements illustrated in FIG. 22 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 208 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 208 can also include a web server for generating and/or delivering the web pages to client computer systems.

In an exemplary embodiment, the computer system 208 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

The computer system 208 can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

Embodiments disclosed herein include:

A. A method that includes advancing an end effector of a surgical tool to a surgical site, the surgical tool being pivotably mounted to a robotic arm at a tool driver, engaging tissue at the surgical site with the end effector, calculating a force vector assumed on the end effector by engaging the tissue, optimizing the force vector to obtain an optimized force vector, and actuating the end effector after applying the optimized force vector on the end effector.

B. A method that includes advancing an end effector of a surgical tool to a surgical site, capturing images of the end effector and the surgical site with an image capture device and displaying the images on a visual display, grasping tissue between opposing jaws of the end effector, calculating a force vector assumed on the end effector, and augmenting the visual display with a computer-generated force indicator graphically coupled to the end effector at a reference point, wherein the force vector forms part of the force indicator and graphically displays magnitude and direction of loading assumed on the end effector.

Each of embodiments A and B may have one or more of the following additional elements in any combination: Element 1: further comprising capturing images of the end effector and the surgical site with an image capture device, displaying the images on a visual display, augmenting the visual display with a computer-generated force indicator graphically coupled to the end effector at a reference point, wherein the force vector forms part of the force indicator and extends from the reference point to graphically display magnitude and direction of loading assumed on the end effector. Element 2: further comprising generating a three-dimensional (3D) model of the end effector and the surgical site displayed on the visual display with a computer system; manipulating an orientation of the 3D model on the visual display to obtain an alternate view of the end effector and the surgical site, and thereby obtaining an alternate view of the force indicator and the force vector. Element 3: wherein optimizing the force vector comprises manipulating one or more user input devices in communication with the computer system, programming the computer system in response to input signals provided by the one or more user input devices, and operating at least one of the robotic arm and the surgical tool with the computer system to move the end effector and obtain the optimized force vector. Element 4: wherein operating the at least one of the robotic arm and the surgical tool with the computer system occurs in real-time as the one or more user input devices are manipulated. Element 5: further comprising scaling down movement of the end effector based on the input signals provided by the one or more user input devices. Element 6: further comprising maintaining the optimized force vector on the end effector while the end effector is actuated. Element 7: wherein optimizing the force vector comprises inputting a desired magnitude and direction for the optimized force vector into a computer system, and operating at least one of the robotic arm and the surgical tool with the computer system to obtain the optimized force vector. Element 8: wherein the robotic arm has a plurality of linkages pivotably coupled at corresponding joints, and wherein calculating the force vector comprises obtaining loading data from one or more sensors positioned in one or both of the tool driver and the corresponding joints, aggregating the loading data with a computer system, and determining with the computer system a magnitude and a direction of the force vector based on the loading data and using inverse kinematics. Element 9: wherein the robotic arm has a plurality of linkages pivotably coupled at corresponding joints, the method further comprising experiencing inadvertent movement of the robotic arm, and actuating one or more actuators positioned in one or more of the tool driver and the corresponding joints and thereby neutralizing movement of the end effector. Element 10: further comprising preventing actuation of the end effector until the optimized force vector is obtained. Element 11: wherein engaging tissue at the surgical site with the end effector comprises grasping the tissue between opposing jaws of the end effector, and wherein the force vector corresponds to tension in the tissue. Element 12: wherein optimizing the force vector comprises advancing one or more additional end effectors to the surgical site, grasping the tissue with the one or more additional end effectors, and maneuvering the one or more additional end effectors to alter the force vector and thereby obtain the optimized force vector. Element 13: wherein the end effector comprises opposing jaws to engage tissue, and optimizing the force vector comprises advancing one or more additional end effectors to the surgical site, grasping the tissue at the surgical site with the one or more additional end effectors, maneuvering the one or more additional end effectors and thereby increasing a tension of the tissue, maneuvering the end effector against the tissue such that a downward load is applied on the tissue with one of the opposing jaws, and actuating the end effector to produce a surgical treatment to the grasped tissue.

Element 14: further comprising optimizing the force vector to obtain an optimized force vector, and actuating the end effector after applying the optimized force vector on the end effector. Element 15: wherein optimizing the force vector comprises manipulating one or more user input devices in communication with the computer system, programming the computer system in response to input signals provided by the one or more user input devices, and operating at least one of the robotic arm and the surgical tool with the computer system to move the end effector and obtain the optimized force vector. Element 16: further comprising observing changes in real-time to the force vector displayed on the visual display as the one or more user input devices are manipulated. Element 17: wherein optimizing the force vector comprises advancing one or more additional end effectors to the surgical site, grasping the tissue with the one or more additional end effectors, and maneuvering the one or more additional end effectors to alter the force vector and thereby obtain the optimized force vector. Element 18: wherein the end effector comprises opposing jaws to engage tissue, and optimizing the force vector comprises advancing one or more additional end effectors to the surgical site, grasping the tissue at the surgical site with the one or more additional end effectors, maneuvering the one or more additional end effectors and thereby increasing a tension of the tissue, maneuvering the end effector against the tissue such that a downward load is applied on the tissue with one of the opposing jaws, and actuating the end effector to produce a surgical treatment to the grasped tissue.

By way of non-limiting example, exemplary combinations applicable to A and B include: Element 1 with Element 2; Element 3 with Element 4; Element 3 with Element 5; Element 11 with Element 12; Element 14 with Element 15; Element 15 with Element 16; and Element 16 with Element 17.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A method, comprising:
    advancing an end effector of a surgical tool to a surgical site, the surgical tool being pivotably mounted to a robotic arm at a tool driver, and the robotic arm having a plurality of linkages pivotably coupled at corresponding joints;
    engaging tissue at the surgical site with the end effector;
    obtaining and aggregating loading data from sensors in one or both of the tool driver and the corresponding joints and thereby calculating a magnitude and a direction of loading on the end effector through engagement with the tissue;
    calculating a force vector assumed on the end effector based on the magnitude and the direction of the loading data;
    optimizing the force vector to obtain an optimized force vector; and
    actuating the end effector after applying the optimized force vector on the end effector.

2. The method of claim 1, further comprising:
    capturing images of the end effector and the surgical site with an image capture device;
    displaying the images on a visual display; and
    augmenting the visual display with a computer-generated force indicator graphically coupled to the end effector at a reference point,
    wherein the force vector forms part of the force indicator and extends from the reference point to graphically display magnitude and direction of loading assumed on the end effector.

3. The method of claim 2, further comprising:
    generating a three-dimensional (3D) model of the end effector and the surgical site displayed on the visual display with a computer system; and
    manipulating an orientation of the 3D model on the visual display to obtain an alternate view of the end effector and the surgical site, and thereby obtaining an alternate view of the force indicator and the force vector.

4. The method of claim 1, wherein optimizing the force vector comprises:
    manipulating one or more user input devices in communication with a computer system;
    programming the computer system in response to input signals provided by the one or more user input devices; and
    operating at least one of the robotic arm and the surgical tool with the computer system to move the end effector and obtain the optimized force vector.

5. The method of claim 4, wherein operating the at least one of the robotic arm and the surgical tool with the computer system occurs in real-time as the one or more user input devices are manipulated.

6. The method of claim 4, further comprising scaling down movement of the end effector based on the input signals provided by the one or more user input devices.

7. The method of claim 1, further comprising maintaining the optimized force vector on the end effector while the end effector is actuated.

8. The method of claim 1, wherein optimizing the force vector comprises:
    inputting a desired magnitude and direction for the optimized force vector into a computer system; and
    operating at least one of the robotic arm and the surgical tool with the computer system to obtain the optimized force vector.

9. The method of claim 1, wherein calculating the force vector further comprises:
    aggregating the loading data with a computer system; and
    determining with the computer system the magnitude and the direction of the force vector using inverse kinematics.

10. The method of claim 1, wherein the robotic arm has a plurality of linkages pivotably coupled at corresponding joints, the method further comprising:
    experiencing inadvertent movement of the robotic arm; and
    actuating one or more actuators positioned in one or more of the tool driver and the corresponding joints and thereby neutralizing movement of the end effector.

11. The method of claim 1, further comprising preventing actuation of the end effector until the optimized force vector is obtained.

12. The method of claim 1, wherein engaging tissue at the surgical site with the end effector comprises grasping the tissue between opposing jaws of the end effector, and wherein the force vector corresponds to tension in the tissue.

13. The method of claim 12, wherein optimizing the force vector comprises:
    advancing one or more additional end effectors to the surgical site;
    grasping the tissue with the one or more additional end effectors; and
    maneuvering the one or more additional end effectors to alter the force vector and thereby obtain the optimized force vector.

14. The method of claim 1, wherein the end effector comprises opposing jaws to engage tissue, and optimizing the force vector comprises:
    advancing one or more additional end effectors to the surgical site;
    grasping the tissue at the surgical site with the one or more additional end effectors;
    maneuvering the one or more additional end effectors and thereby increasing a tension of the tissue;
    maneuvering the end effector against the tissue such that a downward load is applied on the tissue with one of the opposing jaws; and actuating the end effector to produce a surgical treatment to the grasped tissue.

15. A method, comprising:
advancing an end effector of a surgical tool to a surgical site;
capturing images of the end effector and the surgical site with an image capture device and displaying the images on a visual display;
grasping tissue between opposing jaws of the end effector;
calculating a force vector assumed on the end effector;
augmenting the visual display with a computer-generated force indicator graphically coupled to the end effector at a reference point, wherein the force vector forms part of the force indicator and graphically displays magnitude and direction of loading assumed on the end effector; and
moving the end effector and observing changes in real-time to the force vector displayed on the visual display based on movement of the end effector.

16. The method of claim 15, further comprising:
optimizing the force vector to obtain an optimized force vector; and
actuating the end effector after applying the optimized force vector on the end effector.

17. The method of claim 16, wherein the surgical tool is pivotably mounted to a robotic arm at a tool driver, and wherein optimizing the force vector comprises:
manipulating one or more user input devices in communication with a computer system;
programming the computer system in response to input signals provided by the one or more user input devices; and
operating at least one of the robotic arm and the surgical tool with the computer system to move the end effector and obtain the optimized force vector.

18. The method of claim 17, comprising observing changes in real-time to the force vector displayed on the visual display as the one or more user input devices are manipulated.

19. The method of claim 15, wherein optimizing the force vector comprises:
advancing one or more additional end effectors to the surgical site;
grasping the tissue with the one or more additional end effectors; and
maneuvering the one or more additional end effectors to alter the force vector and thereby obtain the optimized force vector.

20. The method of claim 15, wherein the end effector comprises opposing jaws to engage tissue, and optimizing the force vector comprises:
advancing one or more additional end effectors to the surgical site;
grasping the tissue at the surgical site with the one or more additional end effectors;
maneuvering the one or more additional end effectors and thereby increasing a tension of the tissue;
maneuvering the end effector against the tissue such that a downward load is applied on the tissue with one of the opposing jaws; and
actuating the end effector to produce a surgical treatment to the grasped tissue.

\* \* \* \* \*